United States Patent
Siman

(10) Patent No.: US 12,085,565 B2
(45) Date of Patent: *Sep. 10, 2024

(54) SNTF IS A BLOOD BIOMARKER FOR THE DIAGNOSIS AND PROGNOSIS OF SPORTS-RELATED CONCUSSION

(71) Applicant: The Trustees of the University of Pennsylvania, Philadelphia, PA (US)

(72) Inventor: Robert Siman, Wilmington, DE (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/934,837

(22) Filed: Mar. 23, 2018

(65) Prior Publication Data

US 2018/0217142 A1 Aug. 2, 2018

Related U.S. Application Data

(63) Continuation of application No. 14/537,642, filed on Nov. 10, 2014, now Pat. No. 9,952,214, which is a continuation-in-part of application No. PCT/US2014/027716, filed on Mar. 14, 2014.

(60) Provisional application No. 61/792,420, filed on Mar. 15, 2013.

(51) Int. Cl.
*G01N 33/566* (2006.01)
*G01N 33/68* (2006.01)

(52) U.S. Cl.
CPC ....... *G01N 33/566* (2013.01); *G01N 33/6896* (2013.01); *G01N 2333/47* (2013.01); *G01N 2333/4703* (2013.01); *G01N 2800/28* (2013.01); *G01N 2800/2871* (2013.01); *G01N 2800/50* (2013.01); *G01N 2800/52* (2013.01)

(58) Field of Classification Search
CPC ............. G01N 33/566; G01N 33/6896; G01N 2333/4703; G01N 2333/47; G01N 2800/28; G01N 2800/2871; G01N 2800/50; G01N 2800/52

See application file for complete search history.

(56) References Cited

U.S. PATENT DOCUMENTS 9,952,214 B2 4/2018 Simon
11,761,959 B2 * 9/2023 Siman ................ G01N 33/6896
435/6.12

2007/0003982 A1 1/2007 Hayes et al.
2011/0082203 A1 4/2011 Wang et al.
2011/0199084 A1 8/2011 Hasan et al.
2012/0149042 A1 6/2012 Jackowski et al.

FOREIGN PATENT DOCUMENTS

WO WO 2013/020136 2/2013

OTHER PUBLICATIONS

Siman et al., "Evidence that the blood biomarker SNTF predicts brain imaging changes and persistant cognitive dysfunction in mild TBI patients", Frontiers in Neurology, vol. 4, 190, Nov. 2013, pp. 1-8.
Siman et al., "A panel of neuron-enriched proteins as markers for traumatic brain injury in humans", Journal of Neurotrauma, vol. 26, No. 11, Nov. 2009, pp. 1867-1877.
Siman et al., "Biomarker evidence for mild central nervous system injury after surgically-induced circulation arrest", Brain Research, vol. 1213, Jun. 2008, pp. 1-11.
Ling et al., "Biomarkers of increased diffusion anisotropy in semi-acute mild traumatic brain injury: a longitudinal perspective", Brain, Apr. 2012, vol. 135, No. 4, pp. 1281-1292.
Roberts-Lewis et al., "Immunolocalization of calpain I-mediated spectrin degradation to vulnerable neurons in the ischemic gerbil brain", J Neurosci. Jun. 1994;14(6):3934-44.
Shahim et al., "Blood biomarkers for brain injury in concussed professional ice hockey players", JAMA Neurol. Jun. 2014;71(6):684-92.
Kay et al., "Definition of mild traumatic brain injury", J Head Trauma Rehabil 1993; 8(3): pp. 86-87.
Extended EP Search report dated Oct. 9, 2018 from corresponding EP Application No. 18171257.1.

* cited by examiner

*Primary Examiner* — Olga N Chernyshev
(74) *Attorney, Agent, or Firm* — Mark S. Cohen; PEARL COHEN ZEDEK LATZER BARATZ LLP

(57) ABSTRACT

The invention relates to methods for providing prognosis, diagnosis, monitoring and treatment of a mild traumatic brain injury (mTBI) in a subject, including a sports-related concussion. The invention further relates to assessing the severity of brain damage resulting from mTBI in a subject, including in a subject who has not undergone a CT scan following the injury. For example, the methods of the invention can be used to determine the suitability for someone who has suffered a sports-related injury to return to play that sport. This invention also relates to methods of predicting risk for developing brain damage and long-term dysfunction in a subject having suffered mTBI.

40 Claims, 2 Drawing Sheets

Specification includes a Sequence Listing.

SNTF IS A BLOOD BIOMARKER FOR THE DIAGNOSIS AND PROGNOSIS OF SPORTS-RELATED CONCUSSION

CROSS REFERENCE TO RELATED APPLICATIONS

This application is a Continuation of U.S. patent application Ser. No. 14/537,642, filed on Nov. 10, 2014, which is a Continuation-In-Part application of PCT International Application No. PCT/US14/27716, International Filing Date Mar. 14, 2014, claiming priority to and the benefit of U.S. Patent Application 61/792,420, filed Mar. 15, 2013, which are incorporated by reference herein in their entireties.

GOVERNMENT INTEREST

This invention was made with government support under Grant Number P01 NS056202 awarded by the National Institutes of Health. The government has certain rights in the invention.

FIELD OF THE INVENTION

The invention relates to methods for providing prognosis, diagnosis, and treatment for a mild traumatic brain injury (mTBI) in a subject, including sports-related concussion. The invention further relates to monitoring the severity of brain damage resulting from mTBI in a subject and determining the prognosis of a subject that has suffered from mTBI. This invention also relates to methods of predicting who is at risk for developing brain damage and long-term dysfunction.

BACKGROUND OF THE INVENTION

Mild traumatic brain injury (mTBI), alternatively referred to as concussion, is the most common neurological injury and affects over 1.5 million children and adults each year in the United States alone, and hundreds of thousands of military personnel worldwide. mTBI is of increasing concern for participants in contact sports. For athletes and other mTBI sufferers, post-concussion symptoms commonly resolve within hours or days, but for a small proportion of cases brain dysfunction and disability can persist, sometimes for a year or longer. For athletes, challenges remain to make neurobiologically-informed decisions on suitability for return to play and vulnerability to repetitive injuries.

mTBI is typically undetectable with computerized tomography (CT), yet can elicit long-term and clinically significant brain dysfunction in approximately 15-30% of cases. Histopathological and biomechanical findings in experimental animal models and human cases that have come to autopsy suggest that the main underlying structural correlate for long-term functional impairment after mTBI is diffuse axonal injury (DAI), resulting from head rotational acceleration at the moment of injury. Developing neuroradiological methods such as diffusion tensor imaging (DTI) have shown promise for the detection of white matter structural abnormalities after mTBI, but collectively these studies have yielded inconsistent results. Consequently, new approaches are urgently needed for the rapid identification of mTBI patients at risk of developing brain damage and persistent disability.

Blood-based biomarkers for brain damage have long been evaluated as potential prognostic measures in mTBI, but none has emerged thus far as a means of identifying at an early and potentially treatable stage those cases of mTBI with evolving brain damage leading to long-term dysfunction. For example, a number of proteins expressed predominantly in the nervous system become detectable in the blood during the acute post-injury period in some mTBI cases, including the astrocyte-enriched proteins S100β and glial fibrillary acidic protein (GFAP), along with the neuron-enriched neuron-specific enolase (NSE), ubiquitin C-terminal hydrolase L1 (UCH-L1), αII-spectrin C-terminal fragments and a proteolytic fragment of tau. Unfortunately, none of these markers has a prognostic relationship with patient outcomes for mTBI with negative head CT findings.

Blood levels of these markers for brain damage are reportedly elevated following injuries categorized as mild based on clinical examinations using the Glasgow Coma Scale. However, these studies have focused predominantly on TBI cases that also show head CT abnormalities, and based on the positive CT findings these patients would be diagnosed with moderate TBI or "complicated" mTBI at most centers. Positive CT findings are known to be associated with poorer long-term outcomes after TBI, and the presence of intracranial hemorrhages suggests that the blood-brain barrier exhibits at least transient permeability that could impact blood-based biomarker measures. Unfortunately, for the much more common instances of CT-negative mTBI, which includes the vast majority of sports-related concussions, blood-based markers for brain injury have yet to be discovered that are strong predictors of structural damage and long-term functional outcome.

Therefore, there is a need in the art for neurodegeneration biomarkers released from degenerating neurons that are indicative of CT-negative mTBI. As well, there is a need in the art for neurodegneration biomarkers released from degenerating neurons that are indicative of mTBI, when evaluation by CT-scan is not available or has not been performed. This need is especially acute for subjects participating in sport activities. The present invention addresses these needs by providing methods for using calpain-cleaved αII-spectrin N-terminal fragment (SNTF) as a mechanism-based marker for the diffuse axonal injury that underlies brain functional impairment after mTBI/concussion.

SUMMARY OF THE INVENTION

Methods are provided herein for providing a prognosis, diagnosis or severity assessment for a subject having suffered from a mild traumatic brain injury (mTBI) or a suspected concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the mTBI or suspected concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the subject is provided with a prognosis, diagnosis or severity assessment without performing a computerized tomography (CT) scan on the subject following the injury. In some embodiments, the mild traumatic brain injury (mTBI) is a sports-related concussion.

In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored for response to a therapy for the injury) by repeating the methods described herein at various times (e.g., prior to and during therapy for the injury). In some embodiments, the methods include treating the subject for the mTBI or suspected concussion based on the prognosis, diagnosis or severity assessment provided.

In one aspect, methods are provided herein for providing a prognosis, diagnosis or severity assessment for a subject having suffered from a mild traumatic brain injury (mTBI) or a suspected concussion without performing a computerized tomography (CT) scan on the subject, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the mTBI or suspected concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the mild traumatic brain injury (mTBI) is a sports-related concussion. In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored for response to a therapy for the injury) by repeating the methods described herein at various times (e.g., prior to and during therapy for the injury). In some embodiments, the methods include treating the subject for the mTBI or suspected concussion based on the prognosis, diagnosis or severity assessment provided.

In another aspect, methods are provided herein for providing a prognosis, diagnosis or severity assessment for a subject having suffered from a sports-related concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the sports-related concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the subject is provided with a prognosis, diagnosis or severity assessment without performing a computerized tomography (CT) scan on the subject following the sports-related concussion. In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored to determine when it is suitable for the subject to return to play the sport) by repeating the methods described herein at various times. In some embodiments, the methods include treating the subject for the mTBI or suspected concussion based on the prognosis, diagnosis or severity assessment provided.

Methods are provided herein for determining or assessing the risk of brain damage, mTBI-associated abnormality in white matter structure, or long-term functional disability in a subject having suffered from a mild traumatic brain injury (mTBI) or a suspected concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a determination or risk assessment of brain damage or long-term functional disability in in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

Methods are provided herein for providing a prognosis, diagnosis or severity assessment or for monitoring response to therapy for a subject having suffered from a computerized tomography (CT)-negative mild traumatic brain injury (mTBI), the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of or monitoring response to therapy for the mTBI in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex. In some embodiments, the methods include treating the subject for mTBI based on the prognosis, diagnosis or severity assessment provided or the monitoring of the therapy.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
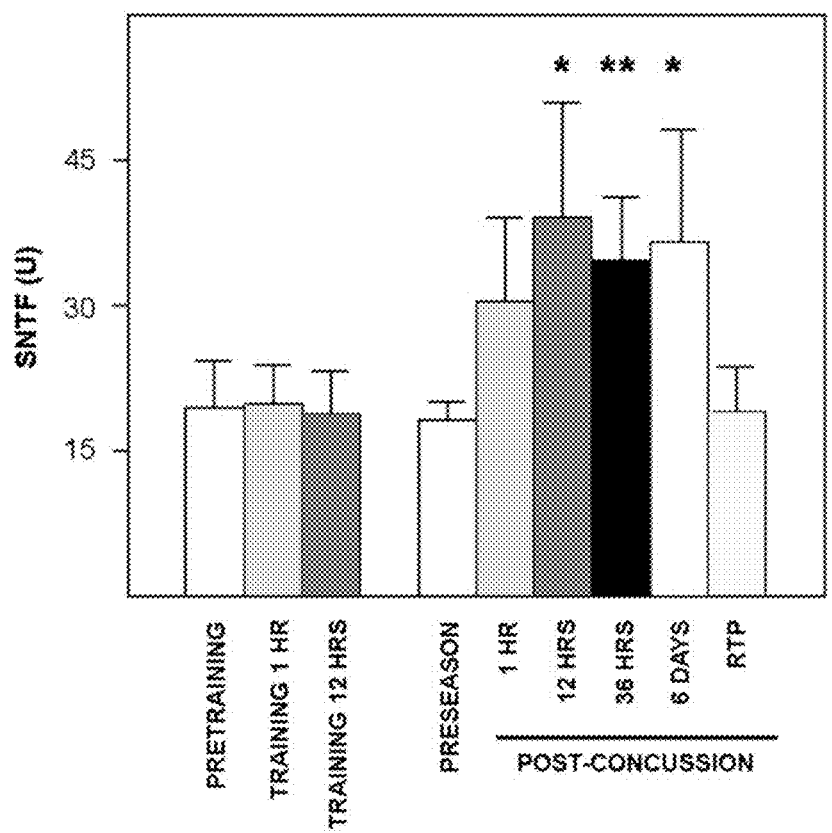
FIG. 1. Sustained increase in serum SNTF concentrations in professional ice hockey players after concussion but not concussion-free training. SNTF levels were measured in serum during the preseason (n=45) or serially after an in-game concussion (n=28), or before and after a training game (n=17). The mean serum SNTF levels (Units+/− S.E.M.) were elevated at 1, 12, 36, and 144 hours post-concussion compared with the mean preseason baseline concentration, and the increases at the latter three time points were statistically significant (two-tailed t-test; *$p<0.03$; **$p<0.002$). At the time of return to play (RTP) after a period of rest, SNTF levels returned to their preseason baseline. In contrast to the pronounced effects of concussion, SNTF was unchanged 1 or 12 hours after concussion-free training ($p>0.87$).

Methods are provided herein for providing a prognosis, diagnosis or severity assessment for a subject having suffered from a mild traumatic brain injury (mTBI) or a suspected concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the mTBI or suspected concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the subject is provided with a prognosis, diagnosis or severity assessment without performing a computerized tomography (CT) scan on the subject following the injury. In some embodiments, the mild traumatic brain injury (mTBI) is a sports-related concussion. In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored for response to a therapy for the injury) by repeating the methods described herein at various times (e.g., prior to and during therapy for the injury). In some embodiments, the methods include treating the subject for the mTBI or suspected concussion based on the prognosis, diagnosis or severity assessment provided.

In one aspect, methods are provided herein for providing a prognosis, diagnosis or severity assessment for a subject having suffered from a mild traumatic brain injury (mTBI) or a suspected concussion without performing a computerized tomography (CT) scan on the subject, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the mTBI or suspected concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the mild traumatic brain injury (mTBI) is a sports-related concussion. In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored for response to a therapy for the injury) by repeating the methods described herein at various times (e.g., prior to and during therapy for the injury). In some embodiments, the methods include treating the subject for the mTBI or suspected concussion based on the prognosis, diagnosis or severity assessment provided.

In another aspect, methods are provided herein for providing a prognosis, diagnosis or severity assessment for a subject having suffered from a sports-related concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of the sports-related concussion in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

In some embodiments, the subject is provided with a prognosis, diagnosis or severity assessment without performing a computerized tomography (CT) scan on the subject following the sports-related concussion. In some embodiments, the methods include determination of the suitability for the subject (e.g., an athlete, such as an amateur or professional athlete) who has suffered the sports-related concussion to return to play that sport. In some embodiments, the methods include determination of or assessing the risk of brain damage and long-term functional disability in the subject. In some embodiments, the subject is monitored (e.g., monitored to determine when it is suitable for the subject to return to play the sport) by repeating the methods described herein at various times. In some embodiments, the methods include treating the subject for the mTBI or suspected concussion based on the prognosis, diagnosis or severity assessment provided.

Methods are provided herein for determining or assessing the risk of brain damage, mTBI-associated abnormality in white matter structure, or long-term functional disability in a subject having suffered from a mild traumatic brain injury (mTBI) or a suspected concussion, the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a determination or risk assessment of brain damage or long-term functional disability in in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex.

Methods are provided herein for providing a prognosis, diagnosis or severity assessment or for monitoring response to therapy for a subject having suffered from a computerized tomography (CT)-negative mild traumatic brain injury (mTBI), the methods include the steps of: (a) obtaining a biological sample from the subject; (b) analyzing the sample to determine the level of a biomarker in the subject, and wherein the biomarker is calpain-cleaved αII-spectrin N-terminal fragment (SNTF); (c) comparing the SNTF level in the subject to that of a pre-determined standard to determine the level of SNTF in the subject relative to the standard; and (d) providing a prognosis, diagnosis or severity assessment of or monitoring response to therapy for the mTBI in the subject, based on the SNTF level in the subject relative to the standard. The step of analyzing the sample may include the steps of (i) contacting said sample with an antibody that specifically binds to SNTF to form an antibody-SNTF complex; and (ii) measuring the amount of the antibody-SNTF complex. In some embodiments, the methods include treating the subject for mTBI based on the prognosis, diagnosis or severity assessment provided or the monitoring of the therapy.

In some embodiments, the subject has not undergone a computerized tomography (CT) scan prior to the prognosis, diagnosis, assessment or treatment. In other embodiments, a CT scan is performed following the comparison of the level of SNTF to the level of the pre-determined standard.

The biological samples may be obtained over a series of time points. For example, at least one sample is collected as soon after a suspected head injury as possible. In some embodiments, a sample is obtained after about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 hours after a suspected head injury as possible. In another embodiment, a sample is collect after about 1 day, about 2 days, about 3 days, about 4 days, about 5 days, or about 6 days after a suspected head injury as possible.

In some embodiments, the standard is determined by measuring the level of the biomarker, such as SNTF, in a subject or pool of subjects having sustained an orthopedic injury or in a normal uninjured subject or pool of subjects. In some embodiments, the standard is taken from a subject or pool of subjects correctly diagnosed as being normal or healthy. In some embodiments, the standard is a baseline level of the marker in the subject. For example, the standard can be the level of the biomarker in the subject prior to a concussion or mTBI. The baseline level or the standard may be below the limit of detection of the assay used to measure the level of the biomarker.

The skilled artisan will appreciate that diagnosing mTBI may permit assesing the risk of mTBI evolving to brain damage and leading to long-term dysfunction. The assessment of the risk of mTBI evolving to long-term dysfunction may permit therapeutic intervention at an early stage. Diagnosing mTBI may permit determining whether or when it is suitability for a sports player, such as a professional athlete, amateur athlete, or recreational player to return to play the sport, return to work, or return to school following an injury.

Brain damage associated with mTBI may be a white matter structural abnormality. The white matter structural abnormality or damage may be in the corpus callosum region, the uncinate fasciculus, the right brain frontal lobe, or the left frontal lobe. The abnormality or damage may be diffuse axonal injury (DAI).

Brain damage can be assessed by neuroimaging techniques and long-term congnitive assessment. For example, the present methods provide for a combined assessment of brain damage including assessing a biomarker (such as SNTF) level (or panel of biomarkers) in a biological sample obtained from a subject having suffered a mTBI, by using diffusion tensor imaging (DTI), computerized tomography (CT) scan imaging, or neuropsychological/behavioral methods. Diffusion tensor imaging (DTI) is known in the art and is used to measure the fractional anisotropy (FA) and the apparent diffusion coefficient (ADC) in a biological tissue. Computerized tomography (CT) scan imaging is also known in the art and it is generally used to provide greater detail than traditional x-rays, particularly of soft tissues and blood vessels. In some embodiments, the subject does not undergo a CT scan following the concussion or injury.

In some embodiments, a concussion is a sports-related concussion. In other embodiments, mTBI is caused by a head injury, where the head injury is blunt trauma, acceleration, or deceleration forces. It will be appreciated that head injuries can be characterized by having one or more of the following conditions: (1) observed or self-reported contusion, disorientation, or impaired consciousness, dysfunction of memory at the time of the injury, or loss of consciousness lasting less than 30 minutes; and (2) symptoms such as headache, dizziness, fatigue, irritability, and poor concentration soon after the injury. Head injuries are also can be categorized as mild based on clinical examinations using the Glasgow Coma Scale. In some embodiments, the head injury has a Glasgow Coma Scale score of 13-15 upon examination at an emergency center, with no abnormal findings on head CT, duration of loss of consciousness for no more than 30 minutes, post-traumatic amnesia for less than 24 hours, and an Abbreviated Injury Score (AIS) S3 and an ISS of <12 modified to exclude the head region.

The level of the biomarker, such as SNTF, in a biological sample obtained from a subject, as provided herein, may be independently associated with mTBI and clinically important parameters in mTBI. The biomarker may indicate the severity of the subject's condition. Thus, comparing the level of the biomarker in the biological sample to the level of the standard permits assessing the severity of mTBI. Sustained levels of the biomarker may be associated with a subsequent increased risk of long-term neurological dysfunction. In addition, the levels of more than one biomarker may be assessed in a biological sample obtained from a subject. For example, the levels of two biomarkers (e.g., SNTF and tau) may indicate the severity of the subject's condition.

The biological sample may be selected from blood, serum, plasma, cerebrospinal fluid (CSF), DNA, tissue biopsy, organ biopsy or a combination thereof.

The SNTF level in the biological sample can be correlated to brain damage and long-term functional disability. Furthermore, levels of SNTF (either alone or in combination with tau) in the biological sample can be correlated to brain damage and long-term functional disability. Comparing the level of the biomarker or a panel of biomarkers in the biological sample to the level of the standard or a pool of standards permits monitoring the response of the therapy. In addition, monitoring response to a therapy further permits adjusting the therapy to reduce the risk of mTBI evolving to brain damage leading to long-term brain dysfunction. Decreasing levels of the biomarker as a result of therapy can indicate a subsequent decreased risk of long-term neurological dysfunction.

In one aspect, provided herein are methods of providing a prognosis for a subject having suffered from a computerized tomography (CT)-negative mild tramatic brain injury (mTBI), the method comprising: obtaining a biological sample from said subject; analyzing the sample to determine the level of a biomarker associated with the presence of mTBI, and comparing the biomarker level to the level of a pre-determined standard, wherein the biomarker is calpain-cleaved αII-spectrin N-terminal fragment (SNTF).

In another aspect, provided herein are methods of providing a prognosis for a subject having suffered from a mild tramatic brain injury (mTBI), the method comprising: obtaining a biological sample from said subject; analyzing the sample to determine the level of a biomarker associated with the presence of mTBI, and comparing the biomarker level to the level of a pre-determined standard, wherein the biomarker is SNTF.

In another aspect, provided herein are methods for identifying a subject at risk of suffering from a mild traumatic brain injury (mTBI)-associated abnormality in white matter structure or a long-term brain dysfunction, the method comprising: obtaining a biological sample from the subject; analyzing the sample to determine the level of a biomarker associated with the presence of mTBI, and comparing said level of said biomarker to the level of a pre-determined standard, wherein the biomarker is SNTF.

In some embodiments, the standard is determined by measuring the level of said biomarker or a pool of biomarkers in a subject having sustained an orthopedic injury or in a normal uninjured subject. In some embodiments, the standard is determined by measuring the level of the biomarker or a pool of biomarkers from the subject prior to the subject suffering the a concussion or mTBI. Comparing the level of a biomarker or pool of biomarkers in the biological sample to the level of the standard or pool of standards permits identifying a subject at risk of suffering from a mild traumatic brain injury (mTBI)-associated abnormality in white matter structure or a long-term brain dysfunction.

The biomarker calpain-cleaved αII-spectrin N-terminal fragment (SNTF) is a marker for mTBI and its blood levels are related to white matter abnormalities and long-term functional disability. Detecting the presence of SNTF in a biological sample obtained from a subject shortly after mTBI is indicative of a risk of developing white matter tract structural damage and long-term disability.

In one embodiment, a second biomarker provided herein is tau. In another embodiment, tau may be used in conjunction with SNTF as a marker for mTBI and their combined blood levels are related to white matter abnormalities and long-term functional disability. In another embodiment, detecting the presence of tau and SNTF in a biological sample obtained from a subject shortly after mTBI indicates a risk of developing white matter tract structural damage and long-term disability.

As demonstrated below (see Examples), blood levels of the neurodegeneration biomarker SNTF identify patients with mTBI likely to have both white matter changes with advanced neuroimaging suggestive of DAI, and also cognitive dysfunction that persists for at least 3 months. Further, as also demonstrated below (see Examples), blood levels of the neurodegeneration biomarker SNTF, either alone or in comnbination with tau, identify patients with mTBI likely to have both white matter changes with advanced neuroimaging suggestive of DAI (see Examples).

Without wishing to be bound by theory, injury-induced elevation in plasma SNTF in mTBI cases is triggered by calpain activation and spectrin degradation within vulnerable axons, which is followed by efflux of the protein fragment into the brain parenchyma and bloodstream in association with the axon tract damage underlying brain functional impairment.

Detecting the presence of neurodegeneration markers in a biological sample obtained from a subject shortly after mTBI indicates risk of developing white matter tract structural damage and long-term disability. Similarly, detecting the presence of neurodegeneration markers in a biological sample obtained from a CT-negative subject shortly after mTBI indicates risk of developing white matter tract structural damage and long-term disability.

Functional variants of SNTF are encompassed by the methods presented here. α-spectrin (alpha chain of non-erythroid spectrin) is a protein that in humans is encoded by the SPTA1 gene. The human SNTF amino acid sequence is the first 1,176 amino acids of the encoded protein and is set forth in SEQ ID NO: 1 Spectrin is an actin crosslinking and molecular scaffold protein that links the plasma membrane to the actin cytoskeleton, and functions in the determination of cell shape, arrangement of transmembrane proteins, and organization of organelles. It is a tetramer of alpha-beta dimers linked in a head-to-head arrangement. This gene is one member of a family of alpha-spectrin genes. The encoded protein is primarily composed of 22 spectrin repeats involved in dimer formation.

(SEQ ID NO: 1)
MDPSGVKVLETAEDIQERRQQVLDRYHRFKELSTLRRQKLEDSYRFQFF

QRDAEELEKWIQEKLQIASDENYKDPTNLQGKLQKHQAFEAEVQANSGA

IVKLDETGNLMISEGHFASETIRTRLMELHRQWELLLEKMREKGIKLLQ

AQKLVQYLRECEDVMDWINDKEAIVTSEELGQDLEHVEVLQKKFEEFQT

DMAAHEERVNEVNQFAAKLIQEQHPEEELIKTKQDEVNAAWQRLKGLAL

QRQGKLFGAAEVQRFNRDVDETISWIKEKEQLMASDDFGRDLASVQALL

RKHEGLERDLAALEDKVKALCAEADRLQQSHPLSATQIQVKREELITNW

EQIRTLAAERHARLNDSYRLQRFLADFRDLTSWVTEMKALINADELASD

-continued

```
VAGAEALLDRHQEHKGEIDAHEDSFKSADESGQALLAAGHYASDEVREK

LTVLSEERAALLELWELRRQQYEQCMDLQLFYRDTEQVDNWMSKQEAFL

LNEDLGDSLDSVEALLKKHEDFEKSLSAQEEKITALDEFATKLIQNNHY

AMEDVATRRDALLSRRNALHERAMRRRAQLADSFHLQQFFRDSDELKSW

VNEKMKTATDEAYKDPSNLQGKVQKHQAFEAELSANQSRIDALEKAGQK

LIDVNHYAKDEVAARMNEVISLWKKLLEATELKGIKLREANQQQQFNRN

VEDIELWLYEVEGHLASDDYGKDLTNVQNLQKKHALLEADVAAHQDRID

GITIQARQFQDAGHFDAENIKKKQEALVARYEALKEPMVARKQKLADSL

RLQQLFRDVEDEETWIREKEPIAASTNRGKDLIGVQNLLKKHQALQAEI

AGHEPRIKAVTQKGNAMVEEGHFAAEDVKAKLHELNQKWEALKAKASQR

RQDLEDSLQAQQYFADANEAESWMREKEPIVGSTDYGKDEDSAEALLKK

HEALMSDLSAYGSSIQALREQAQSCRQQVAPTDDETGKELVLALYDYQE

KSPREVTMKKGDILTLLNSTNKDWWKVEVNDRQGFVPAAYVKKLDPAQS

ASRENLLEEQGSIALRQEQIDNQTRITKEAGSVSLRMKQVEELYHSLLE

LGEKRKGMLEKSCKKFMLFREANELQQWINEKEAALTSEEVGADLEQVE

VLQKKFDDFQKDLKANESRLKDINKVAEDLESEGLMAEEVQAVQQQEVY
```

The level of a biomarker provided herein may be elevated in a biological sample obtained from a patient having suffered mTBI. In another embodiment, the biomarker is expressed in a biological sample obtained from a subject having suffered from mTBI.

Also provided herein are methods for analyzing nucleic acid expression of the biomarkers provided herein. It will be appreciated that the term "nucleic acid" can encompass phosphate ester polymeric forms of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules").

SNTF may be used as either a single or panel of biomarkers for potential clinical diagnosis, risk assessment or prognosis. For example, a panel of biomarkers may include tau and neurofilament polypeptides. Use of a panel of biomarkers may lead to improved risk stratification and the use of directed therapy to modify known factors that are associated with worse outcomes.

The provided methods encompass jointly using a SNTF and an additional neurodegenerative biomarker. The association of SNTF with adverse outcomes can be independent of the additional biomarker. The assessment of the biomarkers jointly may improve risk assessment over either marker alone in subjects with mTBI. In some embodiments, the additional neurodegenerative biomarker is tau.

mTBI may lead to acute brain damage and long-term dysfunction. For example, the long-term dysfunction is a sensory dysfuction. As another example, the dysfunction is a motor dysfunction. As another example, the long-term dysfunction is an emotional or cognitive dysfunction.

Preferably, the subject is a human subject. The subject may suffer a sports-related concussion. In some cases, the subject is a professional sports player; while in orther cases, the subject is a non-professional sports player or an amateur athlete. In some cases, the subject is being monitored for brain damage; while in some cases, the subject is undergoing therapy for brain damage. In some embodiments, the subject with a sports-related concussion is under evaluation to determine suitability to return to play. In some embodiments, the subject has previously suffered from one or more sports-related concussions.

The term "standard" encompasses pooled samples from healthy subjects. The standard may be ethnically- or gender- or age-matched recipients. It is to be understood that the standard may be derived from a subject, or pool of subjects, whose biomarker level profile is sufficient to detect relative differences in biomarker levels, when compared to a test sample, or to a subject that has mTBI with evolving brain damage leading to long-term dysfunction.

In some embodiments, the standard is the average biomarker level of at least one biomarker in a biological sample taken from a pool of subjects. In some embodiments, the standard is the mean biomarker level profile taken from a pool of subjects.

In some embodiments, the standard is the median biomarker level for a biological sample taken from a pool of subjects. In some embodiments, the standard is the median biomarker level of at least one or more biomarkers taken from a pool of subjects. In some cases, a biomarker is not present, present in negligible levels, or below the lower limit of detection in a normal subject.

Measuring/analyzing/quantifying the level of a biomarker provided herein, may be performed using methods know in the art. For example, methods to determine the level of a biomarker include, but are not limited to, PCR, microarray assays, immunoblots, nothern blots, ELISA, fluorescence-based methods (immunofluorescence, FACS), mass spectrometry, and the like.

As used herein, the term "expression" refers to the transcription and stable accumulation of sense (mRNA) or antisense RNA derived from a nucleic acid fragment or fragments. Expression also refers to the translation of mRNA into a polypeptide. Biomarker expression may be tissue-specific. Biomarker expression may be global. Biomarker expression may be systemic.

As used herein, "biological sample" refers to blood, serum, plasma, sperm, urine, mucous, tissue biopsy, organ biopsy, synovial fluid, urine, bile fluid, cerebrospinal fluid, saliva, mucosal secretion, effusion, sweat and combinations thereof. For example, a biological sample may be cells, tissue, peripheral blood, a body fluid and the like. It is understood, that a biological sample includes one obtained from a normal subject.

The proteins of the sample may be distributed on various support matrices by matrix specific methods. Suitable matrices may include paper, cellulose acetate, silica, glass, carbon, sugars, plastics and derivatives thereof, and a person skilled in the art will be familiar with the techniques of using such support matrices for the separation of proteins.

The term "biomarker" is used herein interchangeably with the term "marker." "Marker" in the context of the present invention refers to a polypeptide which is differentially present in a sample taken from subjects having a mTBI, as compared to a comparable sample taken from control subjects (e.g., a person with an orthopedic injury, a healthy subject, or the subject prior to a mTBI).

Determining the expression of a biomarker refers to methods to assess mRNA abundance or gene product abundance. As used herein, a "gene product" refers to the translated protein. Protein abundance reflects gene expression profiles, which may be determined, by methods known in the art, such as, but not limited to Western blot analysis, RIA, ELISA, HPLC, functional assays, such as enzymatic assays, as applicable, and others. An expression profile may be determined by a change in mRNA levels, surface expression, secretion, or other partitioning of a polypeptide.

As used herein, the term "independently associated" refers to an association that is not necessarily causative, e.g., the level of expression of the biomarker or the presence of the biomarker does not need to cause the disease or adverse condition provided herein.

As used herein, "increased expression" or "increase in level or "elevated level" refer to an increase in the level of a biomarker relative to the level or activity of the biomarker in a standard. An increase in level may refer to between a 10 to about a 1000% increase in biomarker levels in a biological sample. The increase of a biological maker level taken from a mTBI subject may be 1-10%, 11-20%, 21-30%, 31-40%, 41-50%, 51-60%, 61-70%, 71-80%, 81-90%, 91-150%, 151-1000% elevated over the levels of that biomarker taken from a normal subject (standard). The increase of a biological maker level taken from a mTBI subject may be detectable when the level of that biomarker taken from a normal subject (standard) is below the lower limit of detection for the assay being used.

As used herein, "compared to a standard", refers to relative changes in biomarker levels where the standard is derived from a single individual, or is derived from pooled subjects, e.g., subjects who have been successfully categorized as being healthy.

As used herein, the term "measuring" refers to methods which include detecting the presence or absence of marker (s) in the sample, quantifying the amount of marker(s) in the sample, and/or qualifying the type of biomarker. Measuring can be accomplished by methods known in the art and those further described herein, including but not limited to SELDI and immunoassay. Any suitable methods can be used to detect and measure one or more of the markers described herein. These methods include, without limitation, mass spectrometry (e.g., laser desorption/ionization mass spectrometry), fluorescence (e.g. sandwich immunoassay), surface plasmon resonance, ellipsometry and atomic force microscopy.

As used herein, the phrase "differentially present" refers to differences in the quantity and/or the frequency of a marker present in a sample taken from subjects having mTBI.

A polypeptide is differentially present between two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between two sets of samples if the frequency of detecting the polypeptide in the subjects' samples is statistically significantly higher or lower than in the control samples. For example, a polypeptide is differentially present between the two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

As used herein, the term "diagnostic" refers to identifying the presence or nature of a pathologic condition, e.g., mTBI.

As used herein, the term "sensitivity" of a diagnostic assay refers to the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay may be calculated as 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker can refer to an amount of a marker present in a sample being tested. A test amount can be either an absolute amount (e.g., µg/mL) or a relative amount (e.g., relative intensity of signals).

A "diagnostic amount" of a marker can refer to an amount of a marker in a subject's sample that is consistent with a diagnosis of a brain damage severity or an adverse condition from an unknown etiology or as a result of mTBI. A diagnostic amount can be either an absolute amount (e.g., 1 µg/mL) or a relative amount (e.g., relative intensity of signals).

A "control amount" or a "standard" amount of a marker can be any amount or a range of amount, which is to be compared against a test amount of a marker. For example, a control amount of a marker can be the amount of a marker in a healthy subject. A control amount can be either an absolute amount (e.g., µg/mL) or a relative amount (e.g., relative intensity of signals).

The methods provided herein include protein level (amount) measurements. The methods provided herein include DNA measurements. The methods provided herein include RNA measurements. The methods provided herein include mRNA measurements. Methods of measuring the expression level of a given protein used as a biomarker are known to one of average skill in the art. Methods of measuring the transcription level of a given RNA molecule encoding a protein used as a biomarker are known to one of average skill in the art. Methods of measuring the transcription level of a given mRNA molecule encoding a protein used as a biomarker are known to one of average skill in the art.

Methods for capturing, analyzing, quantifying, etc., biomarkers are know in the art. Biomarkers can be captured with capture reagents immobilized to a solid support, such as a biochip described herein, e.g., a multiwell microtiter plate or a resin. Once captured on a substrate, e.g., biochip or antibody, any suitable method can be used to measure a marker or markers in a sample. For example, markers can be detected and/or measured by a variety of detection methods including for example, gas phase ion spectrometry methods, optical methods, electrochemical methods, atomic force microscopy and radio frequency methods. Using these methods, one or more markers can be detected. MAP analysis represents a highly quantitative and rapid method for simultaneously analyzing a large number of specific antigens using a very small volume of patient plasma. In another embodiment, analysis of circulating antigen levels within a collected biological sample, via MAP, yields results equivalent to an ELISA assay. In another embodiment, MAP yields results with greater efficiency and with a higher throughput capacity, than an ELISA assay.

If desired, the sample can be prepared to enhance detectability of markers therein. For example, to increase the detectability of markers, a blood serum sample from the subject can be fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the protein of interest can be used. Sample preparations, such as pre-fractionation protocols, are optional and may not be necessary to enhance detectability of markers depending on the methods of detection used. For example, sample preparation may be unnecessary if antibodies that specifically bind markers are used to detect the presence of markers in a sample.

Typically, sample preparation involves fractionation of the sample and collection of fractions determined to contain the biomarkers. Methods of pre-fractionation are known to those of skill in the art and include, for example, size exclusion chromatography, mass spectrometry, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis. Examples of methods of fractionation are described in PCT/US03/00531, but are not limited to, various kinds of chromatography (e.g., anion exchange chromatography, affinity chromatography, sequential extraction, and high performance liquid chromatography) and mass spectrometry. The separation and detection of the proteins in a plasma sample generates a protein spectra for that sample.

Biomarkers in a sample can also be separated by high-resolution electrophoresis, e.g., one or two-dimensional gel electrophoresis. A fraction containing a marker can be isolated and further analyzed by gas phase ion spectrometry. In another embodiment, two-dimensional gel electrophoresis is used to generate two-dimensional array of spots of biomarkers, including one or more markers. See, e.g., Jungblut and Thiede, Mass Spec. Rev. 16:145-162 (1997).

The two-dimensional gel electrophoresis can be performed using methods known in the art. See, e.g., Deutscher ed., Methods In Enzymology vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one-dimensional array are further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures. The pI range of these gels is about 3-10 (wide range gels).

Biomarkers in the two-dimensional array can be detected using suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using a PROTEINCHIP® array) as described herein.

Another method available for use in the present invention is gas chromatography. Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In one embodiment, the biological sample is analyzed for the presence of the biomarker(s). In another embodiment, methods for protein analysis that are known in the art and are available for use in the present invention include, but are not limited to, Mass Spectrometry, Two-Dimensional Electrophoresis Chromatography High Performance Liquid Chromatography, Reversed-Phase Chromatography, Ion Exchange Chromatography, and the like.

An immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

An immunoassay is an assay that uses an antibody to specifically bind an antigen (e.g., a marker). An immunoassay uses specific binding properties of a particular antibody to isolate, target, and/or quantify the antigen. The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a marker from specific species such as rat, mouse, or human can be selected to obtain only those polyclonal antibodies that are specifically immunoreactive with that marker and not with other proteins, except for polymorphic variants and alleles of the marker. This selection may be achieved by subtracting out antibodies that cross-react with the marker molecules from other species.

In another embodiment, provided herein are kits for diagnosing or providing prognosis for a subject developing brain damage as a result of mTBI, comprising equipment including, but not limited to, assays and analytical tools for the assays, both as described herein below in the exemplification, reagents, standards and instructions for analyzing the expression level of two or more biomarkers in a biological sample of the subject.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or PROTEINCHIP® array described above. In one embodiment, the sample is a biological fluid sample taken from a subject. Examples of biological fluid samples include blood, serum, plasma, nipple aspirate, urine, tears, saliva etc. Preferably, the biological fluid comprises blood serum. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxide, alkaline phosphatase and others commonly used in an ELISA), and colorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Methods for measuring the amount of, or presence of, antibody-marker complex include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Electrochemical methods include voltametry and amperometry methods. Radio frequency methods include multipolar resonance spectroscopy. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Immunoassays can be used to determine presence or absence of a marker in a sample, as well as the quantity of a marker in a sample. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

When the sample is measured and data is generated, e.g., by methods described herein such as, but not limited to mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" one and determines the closeness of fit between the two signals. The software also can include code indicating which the test sample is closest to, thereby providing a probable diagnosis.

In some embodiments, multiple biomarkers are measured. The use of multiple biomarkers may increase the predictive value of the test and provide greater utility in diagnosis, categorization of the severity of a subject or patient's condition, patient stratification and patient monitoring. The process called "Pattern recognition" detects the patterns formed by multiple biomarkers and greatly improves the sensitivity and specificity of clinical proteomics for predictive medicine. Subtle variations in data from clinical samples, e.g., obtained using methods provided herein and those known in the art, indicate that certain patterns of protein expression can predict phenotypes such as the presence or absence of a certain disease, a particular stage of a disease, or a positive or adverse response to drug treatments.

As used herein, a protein may have "homology" or be "homologous" to another protein if the two proteins have similar amino acid sequences and have similar biological activities or functions. A protein from two different organisms may have homology or be homologous when the encoded amino acid sequences of the proteins are similar and the proteins have a similar biological activity or function. It is understood that "homologous" does not necessarily imply that there is an evolutionary relationship between the proteins. In one embodiment, a homologous protein exhibits 50% sequence similarity to the wild type protein, or in another embodiment 60% sequence similarity, or in another embodiment 70% sequence similarity. or in another embodiment 80%, 85% or 90% sequence similarity to the wild type protein. or in another embodiment, a homologous protein exhibits 95%, 97%, 98% or 99% sequence similarity.

In one embodiment, the methods of the invention provide for the use of multiple assays, to evaluate differential gene expression. In another embodiment, arrays are used since microarray analysis allows in another embodiment simulataneous gene expression analysis of multiple genes in a high-throughput mode.

A combination of biomarkers may provide greater predictive value than single markers alone. The detection of a plurality of markers in a sample increases the percentage of true positive and true negative diagnoses and would decrease the percentage of false positive or false negative diagnoses. Thus, the methods of the present invention can include the measurement of more than one biomarker.

In other embodiments, the measurement of markers can involve quantifying the markers to correlate the detection of markers with a probable diagnosis of the mTBI or brain damage, as described herein.

The correlation may take into account the amount of the marker or markers in the sample compared to a control amount of the marker or markers (up or down regulation of the marker or markers) (e.g., in normal healthy subjects). A control can be, e.g., the average or median amount of marker present in comparable samples of healthy subjects. The control amount is measured under the same or substantially similar experimental conditions as in measuring the test amount. The correlation may take into account the presence or absence of the markers in a test sample and the frequency of detection of the same markers in a control. The correlation may take into account both of such factors to facilitate determining/practicing the methods provided herein.

Suitable statistical tools, known to one of skill in the art, are used to determine the level of a biomarker relative to a standard.

In one embodiment, continuous measures are described using simple statistics (mean, median, standard deviation, and range) and categorical/ordinal data (e.g. race, gender, and remodeling geometry) with tables and frequencies.

In another embodiment, graphical methods including histograms, scatter plots, and box plots are used to understand aspects of data quality and examine assumptions that underlie parametric and semi-parametric models.

In one embodiment, to better understand the changes in exposure and outcome over time, individual trajectories are plotted as well as group summaries across time, and Kaplan-Meier plots are used to estimate survival probabilities.

In one embodiment the methods provided herein further comprise managing subject treatment based on the status. Such management describes the actions of the physician or clinician subsequent to determining the severity of brain damage. For example, if the result of the methods of the present invention is inconclusive or there is reason that confirmation of status is necessary, the physician may order more tests. Alternatively, if the status indicates that treatment is appropriate, the physician may schedule the patient for treatment. Likewise, if the result is negative, e.g., the status indicates no need for brain damage treatment is needed, no further action may be warranted. Furthermore, if the results show that treatment has been successful, no further management may be necessary. The invention also provides for such methods where the biomarkers (or specific combination of biomarkers) are measured again after subject management. In these cases, the methods are used to monitor the status of the severity of brain damage in a subject. Because of the ease of use of the methods and the lack of invasiveness of the methods, the methods can be repeated after each treatment the patient receives. This allows the physician to follow the effectiveness of the course of treatment. If the results show that the treatment is not effective, the course of treatment can be altered accordingly. This enables the physician to be flexible in the treatment options.

In another example, the methods for detecting markers can be used to assay for and to identify compounds that modulate expression of these markers in vivo or in vitro.

In yet another embodiment, the markers are used in heredity studies to determine if the subject is at risk for developing a more severe case of brain damage.

"Solid support" refers to a solid material which can be derivatized with, or otherwise attached to, a capture reagent. Exemplary solid supports include probes, microtiter plates and chromatographic resins.

"Probe" refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample presenting surface on which an analyte is presented to the source of ionizing energy.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to a component of a sample that is desired to be detected. The term can refer to a single component or a plurality of components in the sample.

The "complexity" of a sample adsorbed to an adsorption surface of an affinity capture probe means the number of different protein species that are adsorbed. "Monitoring" refers to recording changes in a continuously varying parameter.

In one embodiment, provided herein are kits comprising reagents for detecting the biomarker levels, wherein the reagents may include antibodies, nucleic acids, which may hybridize to mRNA isolated from a biological sample, and the like. In one embodiment, reagents may be labelled, or in another embodiment nucleic acids isolated from a biological sample are labelled. In another embodiment, the kit provides instructions for detecting the label qualitatively or quantitatively.

In another embodiment the kit further comprises a buffering agent, a preservative, or a protein stabilizing agent. In one embodiment, the kit further comprises an enzyme or a substrate. In one embodiment, the substrate may be a means of detecting a label, or in another embodiment the expressed protein product itself. In one embodiment, the kit further comprises reagents that are necessary for detection of nucleic acids, amino acids or hybridization signals for nucleic acids.

In one embodiment, detecting differential expression of the genes via the kits of the invention is accomplished using establsihed PCR, ELISA, RIA, and other similarly recognized methods, and the reagents comprise those appropriate for the particular assay for detection.

In one embodiment, the results obtained are compared to a standard, which, in another embodiment, may comprise a series of standards, which, in another embodiment is used in the kits of the invention for quantification of differential levels of the biomarker or differential expression. In one embodiment, the standard may comprise any embodiment listed herein, and in another embodiment, will be suitable for a particular application of the kit. In one embodiment, the standard comprises antibodies for detecting a standard biomarker. In one embodiment, the standard comprises nucleic acids when the kit is used for the determination of nucleic acid profile, or in another embodiment the standard is a protein when the kit is used for the determination of expressed protein profile.

In one embodiment, the kit may be adapted for high-throughput screening, and comprise a microarray.

In one embodiment, the kit further comprise agents, which in another embodiment may comprise antibodies, or other agents which detect activity or in another embodiment expression of the translated protein product. In one embodiment the agents comprise antibodies that detect the presence of specific nucleic acids.

In one embodiment, the kit comprises a microarray, which comprises cRNA of the genes indicated, and others. In one embodiment, the kit may comprise standard oligonucleotide probes, PCR reagents and detectable labels. In another embodiment, the kit may comprise biological samples taken from human subjects. The standard will comprise all embodiments listed herein for the standard, including in one embodiment nucleic acid from pooled samples as provided herein.

In one embodiment, the kit further comprises a positive and negative control, wherein said standards can be assayed and compared to the test sample.

In one embodiment, the kit may further comprise labeled cDNA. Fluorescently labeled cDNA probes may be generated through incorporation of fluorescent nucleotides by reverse transcription of RNA extracted from samples of interest Such methods have been shown to have the sensitivity required to detect rare transcripts, which are expressed at a few copies per cell, and to reproducibly detect at least approximately two-fold differences in the expression.

In one embodiment, the methods of this invention employ probes and primers, which may include repetitive stretches of adenine nucleotides (poly-A tails) normally attached at the ends of the RNA, for the identification of differentially expressed genes. In another embodiment, kits of this invention may comprise such probes.

In one embodiment, the biomarker is a functional biomarker or a functional fragment thereof. In another embodiment, the biomarker is a functional variant or fragment thereof of a biomarker provided herein. In another embodiment the biomarker is a homolog of a biomarker provided herein, where in another embodiment, it is a paralog or an ortholog of a biomarker provided herein.

In one embodimnent, cRNA refers to complementary ribonucleic acid or substantially complementary ribonucleic acid. In another embodiment, cRNA refers to the hybridization or base pairing between nucleotides or nucleic acids, such as, for instance, between the two strands RNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair in one embodiment, with at least about 70% of the nucleotides of the other strand, or in another embodiment with about 90% to 95%, and in another embodiment with about 98 to 100%. The invention also provides a method for treating a mild traumatic brain injury (mTBI) in a subject having a negative computerized tomography (CT) test result. The method includes the prognosis or diagnosis of said mTBI of the invention and, based on the prognosis or diagnosis, treating said mTBI in said subject.

As used herein, the term "treating" may encompass curing, preventing, reducing the incidence of, ameliorating symptoms of, to inducing remission of, or slowing the progression of a disease. The terms "reducing", "suppressing" and "inhibiting" refer to lessening or decreasing.

The term "about" as used herein means in quantitative terms plus or minus 5%, plus or minus 10%, plus or minus 15%, or in another embodiment plus or minus 20%.

The term "subject" refers to a mammal, including a human, in need of therapy for, or susceptible to, a condition or its sequelae. The term "subject" does not exclude an individual that is normal in all respects. The term "patient" is encompassed by the term "subject."

The following examples are presented in order to more fully illustrate the preferred embodiments of the invention. They should in no way be construed, however, as limiting the broad scope of the invention.

EXAMPLES

Materials and Methods

Study Participants. (Examples 1-3)

The Institutional Review Boards of the University of Pennsylvania and Texas Medical Center, Houston, reviewed and approved the study. All participants in this study provided written informed consent (or assent if written consent was given by the minor's parent) and were recruited and assessed with approval from and according to the ethical guidelines of the Institutional Review Boards of the recruiting institutions. All procedures were conducted in accord with the ethical standards of the Helsinki Declaration of 1975, as revised in 2000.

This neurodegeneration biomarker study examined 38 participants with plasma collected within 24 hours of injury. Of those, 17 sustained a mTBI, 13 sustained an orthopedic injury (OI) and 8 were uninjured controls (UC). This effort was part of a larger study (n=205) comprising right-handed participants of ages 12-30 years, who were recruited and tested on neuropsychological and brain imaging measures at baseline (within 96 hours of injury), and at follow-up sessions at 1 month (neuropsychological measures only) and 3 months. Participant recruitment was from an unselected series of patients admitted to emergency centers in the Texas Medical Center, Houston, including Ben Taub General Hospital, Texas Children's Hospital, and Memorial Herman Hospital, or, for the uninjured control group, from the greater Houston metropolitan area. The smaller biomarker study group did not differ significantly from the larger study sample on age, socioeconomic status (SES), race, gender, or extracranial Injury Severity Score (ISS).

The 17 participants providing plasma samples with mTBI, as defined by criteria from the Centers for Disease Control, had an injury to the head from blunt trauma, acceleration, or deceleration forces with one or more of the following conditions: (1) observed or self-reported contusion, disorientation, or impaired consciousness, dysfunction of memory at the time of the injury, loss of consciousness lasting less than 30 minutes; and (2) symptoms such as headache, dizziness, fatigue, irritability, and poor concentration soon after the injury. Additional inclusion criteria were a Glasgow Coma Scale score of 13-15 upon examination at an emergency center, no abnormal findings on head CT, duration of loss of consciousness for no more than 30 minutes, post-traumatic amnesia for less than 24 hours, and an Abbreviated Injury Score (AIS)≤3 and an ISS of <12 modified to exclude the head region. Comparator participants were of two cohorts. For one, participants with 01 were recruited less than 96 hours post-injury provided they met the following criteria: right-handed, 12-30 years old, no loss of consciousness, no post-traumatic amnesia, no overt intracranial injury, AIS<3 for any region of the body and an ISS≤12, and a normal brain CT (if done). A second UC cohort consisted of 8 healthy participants who had not sustained any injury, but were similar to the two injury groups in age, gender and level of education.

Exclusions included non-fluency in either English or Spanish, failure to provide adequate contact information for scheduling follow-up assessments, blood alcohol level>200 mg/dL, previous hospitalization for head injury, pregnancy when screened prior to brain imaging, pre-existing neurologic disorder associated with cerebral dysfunction and/or cognitive deficit (e.g., cerebral palsy, mental retardation, epilepsy) or diagnosed dyslexia, pre-existing severe psychiatric disorder (e.g., bipolar disorder, schizophrenia), and contraindications to undergoing MRI. The OI comparison group was included to control for risk factors that predispose to injury, including preexisting behavioral problems, learning disabilities, and family variables, along with a general trauma context similar to those with mTBI. The uninjured group was included to examine effects not due to injury and to compare injured patients to the general young adult population. All participants provided written informed consent (or assent if written consent was given by the minor's parent) and were recruited and assessed with approval from and according to the ethical guidelines of the recruiting institutions.

Study Participants. (Examples 4-6)

The study was approved by the Ethics Committee for Medical Research at the University of Gothenburg and by the Swedish Ice Hockey Association. Written informed consent was obtained from all 288 study participants comprised of 24 players from each of 12 teams. The physicians for each team documented signs and symptoms of concussion and performed physical examinations in the event of concussion during the first half of the 2012-'13 Ice Hockey season. The diagnosis of concussion (n=28) was made according to the latest guidelines on sports-related concussion. Blood samples were obtained at 1 hour (n=25), 12 hours (n=22), 36 hours (n=20), and 144 hours (n=18) after concussion as well as on the day of return to play (n=10). Physicians recorded the date of concussion and the date at which players completely recovered from their injuries and returned to unrestricted competition. In addition, prior to the start of the season, players from 2 teams were sampled for baseline serum biomarker levels (n=45), and players from 1 of these teams provided blood samples 1 and 12 hours after a training game without concussion incident (n=17).

In Examples 4-6, all 28 hockey players suffering a concussion during the first half of the 2012-'13 Ice Hockey season in the top professional league in Sweden were evaluated, along with 45 players analyzed during the preseason, 17 of whom were also tested before and after a training game without concussion incident. The mean ages were essentially the same for the groups of players tested during the preseason (27.6 years), before and after a training game (27.2 years), or following an in-season concussion (27.2 years). Among the concussion cases, three suffered a loss of consciousness and all experienced post-concussion symptoms including headache, confusion, dizziness, or nausea. Based on grading according to the latest guidelines for sports concussion, eight of the players became symptom-free within a few days of their injury, but in 20 players the symptoms persisted for 6 days or longer. Persistent symptoms that delayed return to play included dizziness, confusion, headache, cognitive impairment, nausea, insomnia, and irritability.

Neurobehavioral Assessments.

Participants were administered tests of cognition and assessed for symptoms related to post-concussive injury. For comparison with neurodegeneration biomarker findings, data was analyzed from three domains, speed of processing, executive memory and cognitive flexibility, along with symptoms of concussion. The analyses were conducted by investigators blinded to the plasma biomarker data.

Rivermead Post Concussion Symptoms Questionnaire (RPCS).

The RPCS is a 16-item self-report of cognitive, emotional, and somatic complaints that are commonly reported following mTBI. Factor analyses have elicited a 3-factor solution comprising cognitive, somatic, and emotional problems, although different factor structures have been reported. The participants were asked to rate the severity of each symptom (currently compared to pre-injury levels) from 0—'not experienced at all' to 4—'severe problem.' The primary variable was the total score.

Symbol-Digit Modalities Test (SDMT).

This is a timed substitution task with written and oral response modalities and is highly sensitive to processing speed deficits in the 8-78 year age range. Using a reference key, each examinee was asked to pair specific numbers with given geometric symbols within 90 seconds. The number of correct responses in the written modality was the variable used in this study.

KeepTrack Task (KT).

This updating task requires adding and deleting items in working memory according to semantic category, and the maintenance of semantic categorical representations. It has been validated in the mild TBI population. The variable used was the mean percent correct items per list recalled.

Diffusion Tensor Imaging.

All participants underwent MRI without sedation on a Philips 3.0 Tesla Achieva scanner. Rigorous quality assurance testing was performed including American College of Radiology phantom testing: no concerns with quality assurance were noted during the course of the study.

An axial single-shot spin-echo echo-planar imaging sequence with 30 diffusion-encoding directions was used for DTI acquisition. Other parameters included a 256 mm field of view, an acquisition voxel size of 2×2×2 mm$^3$, repetition time of 11526 ms, echo time of 51 ms, sensitivity encoding (SENSE) reduction factor of 2, two B factors (0 s/mm$^2$ low B, and 1000 s/mm high B), with two acquisitions to average the signal of the two DTI scans in order to ensure better signal-to-noise ratio. DTI acquisition consisted of 70 slices. A SENSE 8-channel head coil was used.

Image Processing

The corpus callosum, right and left uncinate fasciculi, and right and left frontal lobes were selected as structures of interest due to their known vulnerability in DTI studies of TBI and their presumed relation to the measures of speed of cognitive processing, memory updating, and executive function, and post-concussion symptoms. Additionally, DTI measurement of these structures has been shown to be reproducible both between and within raters on quantitative tractography using previously published protocols. In this study, DTI data were analyzed twice by a single rater to establish intra-rater reliability using intra-class correlational coefficients (ICCs). A subset of the images was analyzed by two raters to establish inter-rater reliability. ICCs for all measurements were above 0.95.

Quantifying the Neurodegeneration Biomarker SNTF (Examples 1-3)

The sandwich immunoassay for quantifying calpain-cleaved αII-spectrin N-terminal fragment (SNTF) from human plasma is a modification of a method published previously, in which the enzymatic amplification and detection steps of ELISA were replaced with electrochemiluminescence detection chemistry. Briefly, 96 well plastic microplates with an underside electrode (Meso Scale Discovery) were coated overnight with the capture antibody, a monoclonal directed at the SH3 domain in the N-terminal portion of the α-spectrin subimit (D8/B7 @ 1/1,000; Abcam). For the antigen capture step, human plasma samples diluted to 40% or SNTF standards (25 μLs/well) prepared in 0.25% bovine serum albumin in Tris-buffered saline (pH 7.4) were added in triplicate for 2 hours at 22° C. The detecting antibody was a purified rabbit IgG prepared in our laboratory and reactive with the calpain-generated neoepitope at the carboxyl-end of the calpain-derived α-spectrin~150 kDa amino-terminal fragment (SNTF; 1/5,000). The specificity of this cleavage site-specific antibody for SNTF has been well established by immunoblot, immunopurification, protease digest, and protease inhibitor experiments. The reporter probe was goat anti-rabbit IgG conjugated to ruthenium (Sulfotag, Meso Scale Discovery, Rockville, MD; 1/500). In the presence of read buffer containing tripropylamine and application of current to the plate electrode, a chemiluminescent product is produced in proportion to the bound antigen. Chemiluminescent signals were quantified by a SECTOR Imager 2400 system (Meso Scale Discovery). Standard curves were generated using serial dilution of a preparation of a-spectrin partially purified from brain and digested with purified calpain I. Briefly, the digestion was performed for 10 minutes at 30° C. at a 300:1 ratio by weight of spectrin extract:calpain I in a buffer of 5 mM Tris-HCl (pH 7.8), 0.6 M KCl, 5 mM β-mercaptoethanol, 2 mM $CaCl_2$. Purified bovine erythrocyte calpain I for the digest was obtained from Sigma (St. Louis, MO). Reactions were quenched and the calpain I inactivated by addition of 5 mM EDTA followed by freeze-thaw.

One unit of SNTF is defined as the signal derived from the SNTF standard diluted to 1 nanoliter per ml, corresponding to ~500 pg of the spectrin-containing brain extract starting material per ml. The minimum reliable detection sensitivity was 10 units.

Control experiments were performed to distinguish SNTF-related signals from non-specific signals emanating from heterophilic substances that are present in a subset of human plasma samples and confound attempts to measure very small amounts of target antigen.

These control immunoassays were conducted as above, except that the detecting IgG specific for SNTF was replaced with normal IgG purified from pre-immune serum from the same rabbit. SNTF-specific signals were calculated as the difference between the specific and pre-immune detecting IgG signals and converted to standardized units. The immunoassays were conducted and analyzed by investigators blinded to all other patient data.

Serum Biomarker (Examples 4-6)

Blood samples were collected and sera prepared by methods known in the art. SNTF was quantified in the de-identified sera using an electrochemiluminescence-based sandwich immunoassay by an experimenter blinded to the data on post-concussion symptom severity and serum levels of the other biomarkers. Briefly, standard 96 well plates with an underside electrode (Meso Scale Discovery) were coated with purified and highly cross-species adsorbed goat anti-mouse IgG (Southern Biotechnology) at 50 ng per well in PBS containing 0.03% Triton X-100, air dried, and stored overnight at 4° C. The next day, wells were blocked with 0.5% bovine serum albumin in TTBS (Tris-buffered saline [pH 7.4] containing 0.05% Tween-20), then washed with TTBS. The capture antibody, a mouse monoclonal to the SH3 domain in the N-terminal half of spectrin αII-subunit (Covance) was applied as ascites fluid at 25 ng per well in 0.2% bovine serum albumin/TTBS for 1 hour, then the wells were washed with TTBS. Next, human sera diluted to 40% or SNTF standards mixed in 0.2% bovine serum albumin/TTBS were added in sextuplicate (25 μl per well) for 2 hours, and then the wells washed with TTBS. A standard curve was generated using a preparation of αII-spectrin isolated from mouse brain membranes by high salt extraction and ammonium sulfate precipitation, followed by digestion with purified erythrocyte calpain I to generate SNTF. The detecting antibody was a cleavage site-specific purified rabbit IgG raised against the calpain-generated neoepitope in the C-terminus of SNTF ending at αII-spectrin residue 1176. This antibody was prepared in the laboratory of the inventors and characterized extensively by Western blotting, immunohistochemistry, protease digest, and solid-phase immunoassay for specific reactivity with SNTF, but not the spectrin holoprotein or other spectrin proteolytic fragments. (Roberts-Lewis, J. L., et al. (1994) *J. Neurosci.* 14:3934; Siman, R., et al. (2009) *J. Neurotrauma* 26:1867) Negative controls were evaluated in triplicate for every serum sample by replacing the SNTF-specific IgG with purified IgG prepared from pre-immune rabbit serum and used at the same concentration (200 ng/ml). The reporter antibody was goat anti-rabbit IgG conjugated to ruthenium (Sulfotag; Meso Scale Discovery), diluted to 1/500 in BSA/TTBS. Following three washes in TTBS, read buffer T containing tripropylamine (Meso Scale Discovery) was added to each well, and using a Sector 6000 system current was applied to the plates and the electrochemiluminescent product generated in each well was quantified. Specific SNTF signal was calculated as the difference in signal between triplicate wells containing either the SNTF IgG or pre-immune IgG, and normalized to brain SNTF standards.

One unit SNTF is defined as the signal generated by 1 nL of the protein standard per mL. The lower limit of detection (LLOD) was determined experimentally to be 14 units.

Tau and S100β were quantified from the sera using methods known in the art. One unit of tau and S100β are defined as the signal generated by their respective protein standards at 1 pg/mL.

Statistical Analyses

For comparison of biomarker levels after concussion or training versus their preseason or pre-training levels, the two-tailed t-test was used. Longitudinal biomarker levels were compared by Mann-Whitney U-test between participants with return to play within less than 6 days and 6 days or greater. Linear regression analyses compared longitudinal post-concussion serum levels of SNTF with tau and S100β. For serum SNTF levels below the lower limit of detection of 14 units, a value of 13 units was assigned for all statistical analyses. The area under the receiver operator characteristics curve (AUC) for SNTF levels post-concussion versus preseason or as a function of the delay in return to play was calculated using GraphPad Prism. Multivariate analyses examined the combination of serum SNTF and tau after concussion in relation to preseason levels and with respect to the delay in return to play, using the statistical methods described above. Equal weighting was placed on SNTF and tau by representing each concentration as a fraction of the mean for that marker, and summing the two fractional means for the combined measure.

Example 1

Changes in Long-Term Cognitive Function in a Subset of mTBI Cases

A total of 38 participants provided plasma samples on the day of injury for quantification of the neurodegeneration biomarker SNTF: 17 were diagnosed with mTBI and 13 with orthopedic injury (OI), whereas 8 were uninjured controls (UC). The biomarker study subgroup did not differ from the overall study group in terms of initial injury severity, age, gender, or other factors (Table 1).

Among these cases, brain structural integrity was assessed by DTI within 4 days of injury for 28 of the participants, and brain performance was evaluated by neuropsychological testing within 4 days of injury and at 1 and 3 months thereafter for 27-29 of the participants, depending on the test battery. The three cohorts did not differ significantly from one another in age, gender, or level of education.

In comparison with OI and UC groups, the mTBI group demonstrated overall performance deficits at 3 months post-injury on the Symbol Digit Modalities Test (SDMT), Keep-Track (KT), and Rivermead Post-Concussion Symptoms Questionnaire (RPCS) cognitive, emotional, and somatic subscales, similar to reports from prior studies. Neuropsychological test performance varied widely among the mTBI participants: some performed indistinguishably from the UC group at both early and late time points, while other participants showed impairments at the acute and/or 1 month time point that resolved by 3 months, and a third set exhibited dysfunction persisting out to 3 months.

Example 2

Plasma SNTF is Elevated in a Subset of mTBI Cases

SNTF was evaluated as a candidate plasma biomarker for human mTBI. This α-spectrin fragment is generated by the calpain family of cysteine proteases and accumulates in axons damaged by stretch injury in vitro or TBI in vivo. It is released from neurons upon plasma membrane disruption. SNTF has not been evaluated before as a prognostic marker in mTBI. Here, plasma SNTF measured on the day of injury was above the lower limit of detection of 10 units in an ultrasensitive sandwich immunoassay in a subset of participants: 7 of 17 mTBI cases and 3 of 13 OI cases. In contrast, plasma SNTF was below the lower limit of detection in all 8 UC participants. The immunoassay signals from the positive plasma samples were confirmed as being specific for SNTF, and not from heterophilic substances that can confound human plasma biomarker studies, by control experiments in which the SNTF-specific detecting IgG was replaced with pre-immune IgG isolated from the same rabbit. The SNTF-positive mTBI participants were both male and female and their injuries spanned a variety of mechanisms from sports, assault, motor vehicle/motorcycle crashes, falls, and being struck by a falling object. Among the SNTF positive participants, the plasma sampling time ranged broadly from 1-24 hours post-injury, and the absolute SNTF levels ranged from 20-150 units. The SNTF positive and negative groups did not differ significantly from one another in age or gender.

Example 3

Elevated Plasma SNTF on the Day of Injury is Related to White Matter Damage and Long-Term Cognitive Dysfunction To examine the relationship between plasma SNTF levels on the day of mTBI and DAI, the 28 participants among the mTBI, OI, and UC cohorts with usable neuroradiological data were dichotomized as either SNTF positive or negative, and the two groups were evaluated comparatively for axon tract structural abnormalities by DTI. Compared with the 19 SNTF negative cases analyzed by DTI within 4 days of injury, the 9 SNTF positive cases exhibited significant reductions in FA and increases in ADC in the corpus callosum and uncinate fasciculus (p<05; Table 2). The FA and ADC are thought to quantify the orientation and structural integrity of white matter, and their differences as a function of dichotomized plasma SNTF levels provide evidence that plasma elevations in this neurodegeneration biomarker after injury may be related to DAI.

TABLE 1

Representativeness of biomarker study subgroup relative to participants in the ongoing mTBI study.

|  | Overall Group Mean (+/−S.D.) (n = 205) | Biomarker Group Mean (+/−S.D.) (n = 38) | P-value |
| --- | --- | --- | --- |
| Age at Baseline | 20.2 (+/−5.4) | 20.5 (+/−5.8) | 0.80 |
| SES | −0.0028 (+/−0.79) | −0.039 (+/−0.72) | 0.80 |
| Race % non Black | 61 | 60 | 0.87 |
| Gender % Female | 33 | 26 | 0.38 |
| GCS (mTBI) % <15 | 23 | 24 | 0.85 |
| Noncranial Injury Severity | 0.93 (+/−1.17) | 1.37 (+/−1.42) | 0.13 |

There were no differences related to demographics or injury between the biomarker study group and the overall study group (t-test).

TABLE 2

Plasma SNTF is related to diffusion tensor imaging differences in select white matter tracts.

| Region/metric | Mean (SD) All SNTF− (n = 19) | Mean (SD) All SNTF+ (n = 9) | P value | Effect Size |
| --- | --- | --- | --- | --- |
| Corpus callosum |  |  |  |  |
| FA | 0.496 (0.02) | 0.479 (0.01) | 0.034 | 0.91 |
| ADC | 0.821 (0.03) | 0.839 (0.02) | 0.13 | 0.63 |
| Uncinate Fasciculus, Left |  |  |  |  |
| FA | 0.405 (0.02) | 0.388 (0.02) | 0.09 | 0.73 |
| ADC | 0.754 (0.03) | 0.775 (0.03) | 0.14 | 0.63 |
| Uncinate Fasciculus, Right |  |  |  |  |
| FA | 0.389 (0.01) | 0.367 (0.02) | 0.001 | 1.48 |
| ADC | 0.774 (0.02) | 0.798 (0.03) | 0.035 | 0.89 |
| Frontal Lobes, Left |  |  |  |  |
| FA | 0.394 (0.02) | 0.383 (0.02) | 0.26 | 0.47 |
| ADC | 0.765 (0.02) | 0.782 (0.02) | 0.07 | 0.77 |
| Frontal Lobes, Right |  |  |  |  |
| FA | 0.382 (0.03) | 0.381 (0.02) | 0.95 | 0.03 |
| ADC | 0.783 (0.02) | 0.794 (0.02) | 0.15 | 0.59 |

Dichotomized plasma SNTF levels on the day of injury discriminate groups on brain white matter structural integrity indexed by diffusion tensor imaging performed within 96 hours. Effect size is reported as Cohen's d, where 0.2-0.49 reflects small, 0.5-0.79 medium, and 0.8 or higher large effect size, and P value is from two-tailed t-test.

Long-term behavioral studies have provided evidence that a subset of CT-negative patients with mTBI develop brain functional disability that can persist for many months post-injury. To examine the prognostic relationship between plasma SNTF levels measured on the day of mTBI and long-term brain function, participants were evaluated within 4 days and again at 1 and 3 months post-injury on a battery of tests for cognitive performance and assessed for post-concussion symptoms. These included the Symbol-Digit Modalities Test (SDMT), which measures speed of cognitive processing and is a sensitive index of cognitive functioning independent of intelligence level, the KeepTrack Task, a measure of memory updating and executive function, and the Rivermead Post-Concussiom Symptoms Questionnaire (RPCS), a self-report assessment of the severity of somatic, emotional and cognitive symptoms after concussion. For groups dichotomized with respect to plasma SNTF levels on the day of injury, there were marked differences in functional measures at both the acute and long-term time points. Plasma SNTF did not discriminate symptomatology on the overall RPCS, but showed an association with impairments in the cognitive and somatic components at 3 months post-injury that did not reach statistical significance. Most importantly, a detectable level of plasma SNTF on the day of injury discriminated test performance at 3 months on the written versions of the SDMT and the KeepTrack task, and the relationship with the former cognitive deficit was highly significant (p<0.01; Table 3).

The significant discrimination in the written and oral versions of the SDMT observed across all study participants based on dichotomized plasma SNTF (Table 3) was even stronger among the mTBI cases by themselves (written SDMT: SNTF+=46.8; SNTF−=59.1; p=0.011; oral SDMT: SNTF+=70.1; SNTF−=53.3; p=0.024).

Plasma SNTF on the day of mTBI also correlated with recovery of cognitive performance Among the 13 mTBI participants evaluated by the oral SDMT in both the acute (1-4 days) and long-term (3 month) post-injury time periods, test scores for the SNTF−cases improved by 17 points (+/−5.7, s.e.m.), whereas those for the SNTF+cases worsened by 2.6 points (+/−2.7). The difference in 3 month recovery of cognitive performance as a function of dichotomized plasma SNTF levels was significant (Table 4; p<0.03). Six of eight SNTF−cases of mTBI showed improvement in cognitive performance over 3 months of 5 points or greater on the oral SDMT, compared with none of the five SNTF+cases). Based on this preliminary post-hoc assessment, plasma SNTF on the day of mTBI showed 100% sensitivity and 75% specificity for predicting failure to improve cognitive performance over the first 3 months after a CT-negative mTBI.

TABLE 3

Plasma SNTF on the day of a mTBI relates to impaired cognitive performance at 3 months post-injury.

| Test | All SNTF+ | All SNTF− | Effect size |
|---|---|---|---|
| Symbol-Digit Modalities Test, Written (total correct responses) | 52.00 (12.1) | 63.47 (14.86) | 0.88 (large) |
| KeepTrack Task (Percent correct recalled) | 88.89 (7.8) | 92.72 (5.6) | 0.63 (mod-large) |
| RiverMead Post-Concussion Symptoms (total score) | 9.44 (10.89) | 6.37 (11.08) | 0.28 (small) |

Dichotomized plasma SNTF levels on the day of injury (+/−SD in parentheses) are related to behavioral differences 3 months post-injury. Effect size is reported in Cohen's d, where 0.2-0.49 reflects a small, 0.5-0.79 a medium, and 0.8 or higher a large effect size. The difference in cognitive performance on the written Symbol Digit Modalities Test across all study participants based on plasma SNTF is significant by two-tailed t-test (p<0.04), as is the difference within the mTBI cases by themselves (SNTF+=46.8; SNTF−=59.1; p<0.025).

TABLE 4

Dichotomized plasma SNTF levels on the day of injury correlate with impaired cognitive performance at 3 months.

| Cognitive performance test | Mean (SEM) SNTF negative | Mean (SEM) SNTF positive | P Value |
|---|---|---|---|
| SDMT at 3 months | | | |
| All study subjects | 63.4 (3.4) | 52.0 (4.0) | 0.039 |
| mTBI cases | 59.1 (2.8) | 46.8 (2.9) | 0.011 |
| ΔSDMT over 3 months | | | |
| mTBI cases | +17.5 (5.7) | −2.6 (2.7) | 0.029 |

The SDMT scores were significantly worse for the biomarker positive cases both across all study participants and among the mTBI cases by themselves (two-tailed t-test). In the mTBI group, elevated SNTF on the day of injury also predicted failure to improve cognitive performance over 3 months.

In this study, evidence has been provided that the blood level of the neurodegeneration biomarker SNTF identifies mTBI patients on the day of their injury likely to have both white matter changes with advanced neuroimaging suggestive of DAI, and also cognitive dysfunction that persists for at least 3 months.

In contrast to the prior findings with other marker candidates, our results indicate that the blood level of SNTF sampled in the acute period after CT-negative mTBI help identify at an early and treatable stage a subset of cases at risk of developing white matter tract structural damage and long-term disability.

The injury-induced elevation in plasma SNTF in a subset of mTBI cases reported here show that functionally impactful mTBI triggers calpain activation and spectrin degradation within vulnerable axons, followed by efflux of the stable fragment SNTF into the brain parenchyma and bloodstream in association with the axon tract damage underlying brain functional impairment.

Increased plasma SNTF post-concussion is related not only to structural evidence for diffuse axonal injury (DAI), but also functional evidence for long-term cognitive impairment. Whereas a subset of the participants with mTBI exhibit no discernible deficits on a battery of cognitive, somatic, or emotional tests post-injury, a second group shows performance deficits that resolve over time, while a third group develops impaired brain performance persisting for at least 3 months post-injury. Strikingly, the dichotomized plasma level of SNTF measured on the day of injury is related to cognitive dysfunction at 3 months, as evidenced by a significant deficit in the SNTF-positive group in the Symbol Digit Modalities Test and trends toward impairments in the KeepTrack test (Table 3) and the cognitive component of the Rivermead Post Concussion Symptoms Questionnaire (RPCS). The ability of plasma SNTF elevations to significantly differentiate long-term cognitive decline holds across all 28 participants in the mTBI, OI, and UC groups and even more strongly among the mTBI cases by themselves. Plasma SNTF on the day of mTBI also discriminated subsequent change in cognitive performance on the Symbol Digit Modalities Test, with a positive SNTF finding predicting failure to improve cognitive performance over 3 months post-injury (Table 4).

Overall, the results show that the blood level of SNTF on the day of a CT-negative mTBI can identify a subset of patients at risk of white matter damage and persistent disability. SNTF can have prognostic and diagnostic utilities in the assessment and treatment of mTBI.

Example 4

Changes in Serum SNTF in Professional Ice Hockey Players Following Concussion

Serum SNTF levels were variable and generally low in samples taken during the preseason, with concentrations being below the lower limit of detection (LLOD) in 58% of the players. The detection of serum SNTF above the lower limit in a subset of experienced professional athletes (levels were at least twice the LLOD in 16% of cases) contrasts with a pilot study of serum SNTF in non-professional athlete healthy controls, whose levels were below the LLOD in 100% of cases.

During the hockey season, serum SNTF concentrations increased in a rapid and prolonged fashion in players who sustained a concussion. The mean SNTF concentration was up to 2-fold higher at 1, 12, 36, and 144 hours post-concussion compared with preseason levels, and the increases at the latter 3 time points were statistically significant (FIG. 1). By the time players were symptom-free and permitted to return to play (RTP), SNTF levels returned to near preseason baseline.

To distinguish the effects of concussion on serum SNTF separate from any influence of physical exertion, the marker was measured serially in 17 players during the preseason and at two time points after a concussion-free training game. In contrast to the pronounced effects of concussion, serum SNTF levels were unchanged at 1 or 12 hours after a training game compared with their pre-game levels. (FIG. 1)

Figure 2:
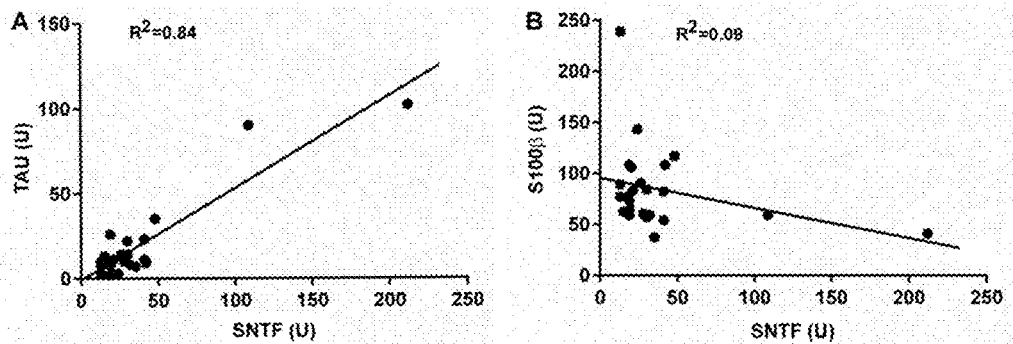
FIG. 2 (A and B). Serum levels of SNTF after concussion are related to serum tau but not S100β. The mean serum SNTF concentration at 12 and 36 hours post-concussion is linearly related to the serum tau concentration measured at 1 hour post-concussion (A), but not to the serum level of S100β at 1 hour (B). For measures of either SNTF or tau at all other time points, the correlation between the two markers is less strong (data not shown). Levels of each marker are represented in units.

Serum concentrations of total tau are elevated in this cohort of concussed professional hockey players relative to preseason and pre-training game levels. Given that tau is an axon-enriched microtubule-associated protein, and SNTF accumulates preferentially in damaged axons after TBI, the serum elevations in these two cytoskeletal proteins may be mechanistically related to one another, and to TBI-induced diffuse axonal injury. To begin assessing this possibility, the serum levels of SNTF and tau were compared on a per-player basis. As shown in FIG. 2 (A), the mean serum SNTF level at 12-36 hours post-concussion was linearly related to serum tau level assessed 1 hour post-concussion ($R^2=0.84$; n=24). The relationship between serum SNTF and tau was less strong when either marker was evaluated at other times after concussion (data not shown). Serum concentrations of the astroglial-enriched S100β are also elevated at 1 hour post-concussion compared to its preseason baseline concentration in this player cohort (Shahim et al., (2014) *JAMA Neural.* 71:684). However, in contrast to the correlation between serum concentrations of SNTF and tau, there was no relationship between serum levels of SNTF and S100β (FIG. 2(B)).

Example 5

Serum SNTF is an Accurate Diagnostic of Sports-Related Concussion

Figure 3:
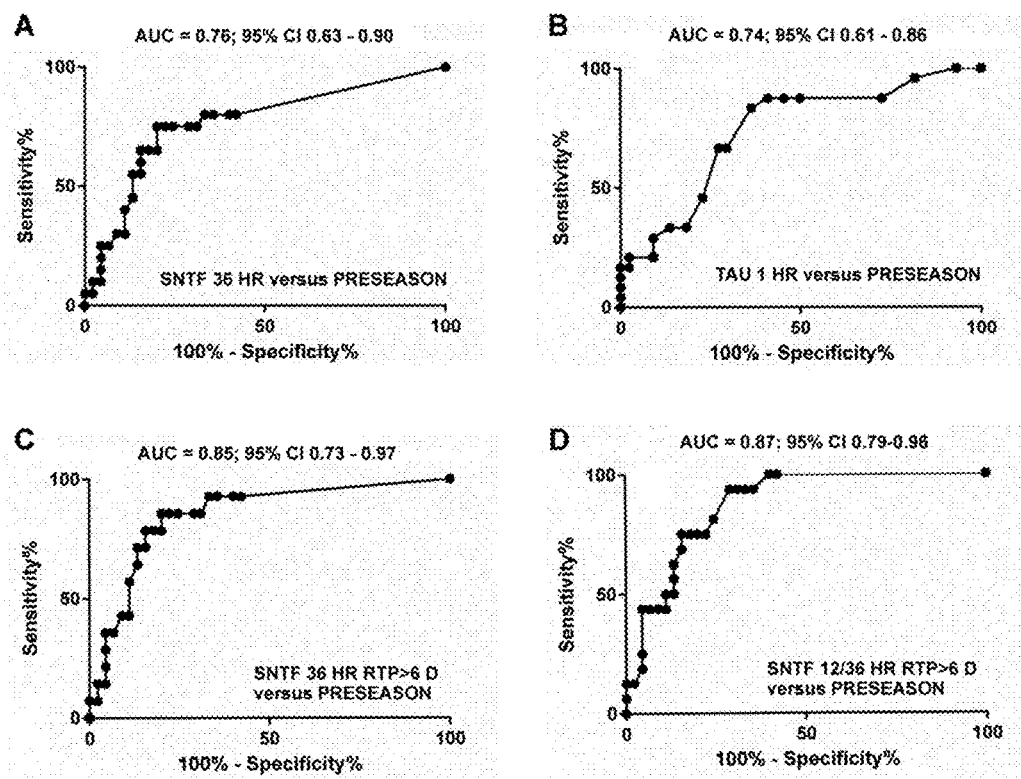
FIG. 3 (A, B, C and D). Diagnostic accuracy of serum SNTF and tau assessed by receiver operator characteristics area under the curve (AUC) analyses. (A) Serum SNTF levels at 36 hours post-concussion versus preseason levels; (B) Serum tau levels at 1 hour post-concussion versus preseason levels; (C) Serum SNTF levels at 36 hours for concussions with return to play>6 days versus preseason levels; (D) Mean serum SNTF levels at 12-36 hours for concussions with return to play>6 days versus preseason levels. AUC: area under the curve; CI: confidence interval.

To assess the accuracy of serum SNTF for the diagnosis of sports-related concussion, the area under the receiver operator characteristics curve (AUC) was analyzed by comparing SNTF levels tested at different times post-concussion with preseason SNTF concentrations. The AUC=0.76 for SNTF 36 hours after concussion versus SNTF during the preseason (FIG. 3(A)), which compares favorably to the AUC for tau various times after concussion versus the preseason (highest AUC=0.74 at 1 hour; FIG. 3 (B)). SNTF at 36 hours showed greater accuracy in diagnosing concussion in players experiencing persistent post-concussion symptoms that delayed the return to play to 6 days or longer (AUC=0.85; FIG. 3(C)). Finally, the AUC=0.87 for the mean serum SNTF at 12-36 hours in players with post-concussion symptoms lasting for at least 6 days compared with preseason biomarker levels (FIG. 3(D)).

Example 6

Serum SNTF is Related to the Severity of Concussion

A fast and objectively quantified blood biomarker test could be valuable for the clinical research and management of sports-related concussion. As described above, the diagnostic accuracy of serum SNTF from 12-36 hours after concussion was especially high for the subset of cases experiencing post-concussion symptoms persisting at least 6 days. To investigate further the relationship between longitudinal measures of serum SNTF and the persistence of post-concussion symptoms, biomarker levels were compared between concussion cases with return to play in less than 6 days with those requiring a delay in return to play of 6 days or longer (Table 5).

TABLE 5

Longitudinal serum SNTF, Tau, and S100β concentrations in relation post-concussion symptom severity.

| Time post-concussion | <6 d RTP | ≥6 d RTP | P value |
| --- | --- | --- | --- |
| SNTF, 1 hour | 20.4 +/− 3.1 (n = 8) | 35.5 +/− 12.9 (n = 16) | 0.98 |
| 12 hours | 19.0 +/− 2.4 (n = 8) | 50.4 +/− 19.0 (n = 14) | 0.087 |
| 36 hours | 19.3 +/− 3.0 (n = 6) | 41.0 +/− 8.4 (n = 14) | 0.014 |
| 12/36 hours | 18.6 +/− 2.1 (n = 8) | 45.8 +/− 11.6 (n = 17) | 0.004 |
| 6 days | 17.0 +/− 4.0 (n = 5) | 44.6 +/− 15.4 (n = 13) | 0.15 |
| Tau, 1 hour | 9.0 +/− 2.1 (n = 8) | 23.1 +/− 7.0 (n = 17) | 0.070 |
| 12 hours | 4.8 +/− 1.8 (n = 8) | 17.9 +/− 7.4 (n = 15) | 0.039 |
| 36 hours | 5.7 +/− 1.6 (n = 7) | 28.0 +/− 12.5 (n = 14) | 0.11 |
| 6 days | 8.0 +/− 1.7 (n = 5) | 35.6 +/− 14.5 (n = 12) | 0.34 |
| S100β, 1 hour | 106 +/− 21 (n = 8) | 72.7 +/− 5.6 (n = 17) | 0.27 |
| SNTF 12/36 + Tau12 | 69 +/− 8 (n = 8) | 224 +/− 65 (n = 17) | 0.011 |

Table 5 presents the serum concentrations of the three markers (mean units+/−S.E.M.) in relation to the severity of post-concussion symptoms, dichotomized on the basis of a delay in return to play (RTP) of <6 days or >6 days. SNTF and tau serum concentrations were higher in the players with more persistent post-concussion symptoms, whereas S100β serum levels were not. The increase in serum SNTF was statistically significant by Mann-Whitney U-test at 36 hours and for the 12-36 hour mean, whereas the elevation in serum tau was statistically significant at 12 hours post-concussion. The multivariate measure of serum SNTF (mean at 12-36 hours) and tau (at 12 hours) was also statistically significant, but at no combination of time points were multi-variate measures of SNTF and tau related more strongly to post-concussion symptom severity than SNTF alone.

At times ranging from 1 hour to 6 days post-concussion, serum SNTF was essentially unchanged from preseason baseline levels for the subset of players with rapidly resolving post-concussion symptoms. In sharp contrast, for cases with persistent post-concussion symptoms lasting 6 days or longer, serum SNTF levels were higher by up to 2.5-fold from 1 hour to 6 days post-injury compared with concentrations either at preseason baseline or in players with less severe post-concussion symptoms. The difference in serum SNTF concentration after concussion as a function of post-concussion symptom severity was significant at the 36 hour time point (p=0.014) and from the mean at 12 and 36 hours (p=0.004). Serum tau levels also were higher in the subset of concussions requiring at least 6 days for return to play compared with cases with shorter-lasting post-concussion symptoms, with the difference at 12 hours being significant (p=0.039).

On the other hand, whereas the serum level of S100β at 1 hour post-concussion was above its preseason baseline concentration, there was no difference in S100β levels between concussions associated with relatively rapid (<6 days) and delayed (≥6 days) return to play.

To determine whether the combined measure of serum SNTF and tau was associated more strongly with post-concussion symptom severity than either marker alone, an equal-weight multivariate analysis was performed. The multivariate measure of two markers across all combinations of time points correlated less strongly with the dichotomized delay in return to play than serum SNTF concentrations alone. The addition of SNTF improved the correlation with post-concussion symptom severity achieved with serum tau alone, and broadened its temporal window (Table 5).

Conclusions Examples 4-6

SNTF was elevated in the serum of professional ice hockey players who suffered a concussion in comparison with its preseason level. Longitudinal analysis found that the serum concentration of SNTF increased as early as 1 hour post-concussion and remained elevated significantly above preseason baseline for up to 6 days thereafter, before returning to baseline at the time of return to play (FIG. 1). The rise in serum SNTF levels was not simply due to the physical exertion of hockey, as the marker was unchanged in players evaluated serially before and after a concussion-free training game.

Perhaps most importantly, serum SNTF related to the severity of the post-concussion symptoms, as assessed by the latest guidelines for sports concussions. For players whose post-concussion symptoms resolved within a few days, serum SNTF levels were essentially unchanged from their preseason baseline. On the other hand, for concussed players with persisting post-concussion symptoms requiring they be withheld from play for 6 days or longer, serum SNTF concentrations were significantly elevated from 12 to 144 hours post-injury compared with preseason baseline, and also from 12-36 hours compared with concussed players whose symptoms resolved within a few days (Table 5; p=0.004). Serum SNTF had accuracy for diagnosing concussions, especially the subset with persisting post-concussion symptoms (FIG. 3 (D); AUC=0.87). These results provide evidence that serum SNTF analyzed subacutely after injury may have utilities for the diagnosis and prognosis of sports-related concussion, and might facilitate objective, neurobiologically-informed decisions on fitness for return to play.

Having described the embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for providing a prognosis for and treating a subject having suffered from a mild traumatic brain injury (mTBI), said method comprising:
   (a) obtaining a blood, serum, or plasma sample from said subject within 36 hours of the injury;
   (b) contacting said sample with an antibody that specifically binds to a calpain-generated neoepitope of calpain-cleaved αII-spectrin N-terminal fragment (SNTF), but not to full-length spectrin, to form an antibody-SNTF complex;
   (c) measuring the amount of the antibody-SNTF complex, to determine SNTF concentration in the subject's blood, serum or plasma;
   (d) comparing the blood, serum or plasma concentration of SNTF in the subject to that of a pre-determined standard;
   (e) providing a prognosis for the subject based on the blood, serum or plasma concentration of SNTF in the subject relative to the standard, wherein an elevated level of SNTF relative to the standard indicates an elevated risk of long-term neurological dysfunction; and
   (f) treating said mTBI in said subject.

2. The method of claim 1, wherein said standard is determined by measuring SNTF levels in a subject or pool of subjects having sustained an orthopedic injury or in a normal uninjured subject or pool of subjects.

3. The method of claim 1, wherein said standard is determined by measuring SNTF levels in a blood, serum, or plasma sample from said subject prior to suffering the mTBI.

4. The method of claim 1, wherein said method further comprises the steps of measuring the level of tau in the sample compared to a standard, and the prognosis provided for the subject is based on the SNTF and tau levels relative to their respective standards, wherein elevated levels of SNTF, tau, or both relative to their respective standards indicate an elevated risk of long-term neurological dysfunction.

5. The method of claim 1, wherein said subject is further assessed by diffusion tensor imaging (DTI).

6. The method of claim 1, wherein said subject is further assessed by neuropsychological testing.

7. The method of claim 1, wherein said subject does not undergo a CT scan following said mTBI.

8. The method of claim 1, wherein said mTBI is a sports-related concussion.

9. The method of claim 1, wherein said mTBI is caused by a head injury, and wherein said head injury is blunt trauma, acceleration, or deceleration forces.

10. The method of claim 8, wherein said subject is a professional sports player.

11. The method of claim 10, wherein providing said prognosis includes determining suitabilty for said sports player to return to play.

12. A method for diagnosing and treating mild traumatic brain injury (mTBI) in a subject having suffered a suspected concussion, said method comprising:
   (a) obtaining a blood, serum, or plasma sample from said subject, within 36 hours of the suspected concussion;
   (b) contacting said sample with an antibody that specifically binds to a calpain-generated neoepitope of calpain-cleaved αII-spectrin N-terminal fragment (SNTF), but not to full-length spectrin, to form an antibody-SNTF complex;

(c) measuring the amount of the antibody-SNTF complex, to determine SNTF concentration in the subject's blood, serum or plasma;

(d) comparing the blood, serum or plasma concentration of SNTF in the subject to that of a pre-determined standard;

(e) diagnosing said mTBI in said subject based on the blood, serum or plasma concentration of SNTF in the subject relative to the standard, wherein an elevated level of SNTF relative to the standard indicates severity of mTBI; and (f) treating said mTBI in said subject.

13. The method of claim 12, wherein said standard is determined by measuring SNTF levels in a subject or pool of subjects having sustained an orthopedic injury or in a normal uninjured subject or pool of subjects.

14. The method of claim 12, wherein said standard is determined by measuring SNTF levels in a blood, serum, or plasma sample from said subject prior to suffering the suspected concussion.

15. The method of claim 12, wherein said method further comprises the steps of measuring the level of tau in the sample compared to a standard, and the diagnosis for the subject is based on the SNTF and tau levels relative to their respective standards, wherein elevated levels of SNTF, tau, or both relative to their respective standards indicate severity of injury.

16. The method of claim 12, wherein said subject does not undergo a CT scan after suffering from the suspected concussion.

17. The method of claim 12, wherein said subject is further assessed by neuropsychological testing.

18. The method of claim 12, wherein said concussion is a sports-related concussion.

19. The method of claim 12, wherein said concussion is caused by a head injury, and wherein said head injury is blunt trauma, acceleration, or deceleration forces.

20. The method of claim 18, wherein said subject is a professional sports player.

21. A method of treating and monitoring a response to that treatment in a subject having suffered from a mild traumatic brain injury (mTBI), said method comprising:

(a) prior to treating said subject, obtaining a blood, serum, or plasma sample from said subject, within 36 hours of the injury;

(b) contacting said sample with an antibody that specifically binds to a calpain-generated neoepitope of calpain-cleaved αII-spectrin N-terminal fragment (SNTF), but not to full-length spectrin, to form an antibody-SNTF complex;

(c) measuring the amount of the antibody-SNTF complex, to determine SNTF concentration in the subject's blood, serum or plasma;

(d) comparing the blood, serum or plasma concentration of SNTF in the subject to that of a pre-determined standard;

(e) treating said mTBI in said subject;

(f) obtaining a blood, serum, or plasma sample from said subject, during or after treatment of said subject for mTBI;

(g) repeating steps (b)-(d), for the sample obtained during or after treatment of said subject; and (h) monitoring the response to the treatment in the subject, wherein sustained elevated SNTF levels indicates a subsequent increased risk of long-term neurological dysfunction.

22. The method of claim 21, wherein said standard is determined by measuring SNTF levels in a subject or pool of subjects having sustained an orthopedic injury or in a normal uninjured subject or pool of subjects.

23. The method of claim 21, wherein said standard is determined by measuring SNTF levels in a blood, serum, or plasma sample from said subject prior to suffering said mTBI.

24. The method of claim 21, wherein said method further comprises the steps of measuring the level of tau in the sample compared to a standard, and monitoring the subject based on the SNTF and tau levels relative to their respective standards, wherein elevated levels of SNTF, tau, or both relative to their respective standards indicate need for further monitoring of the subject.

25. The method of claim 21, wherein said mTBI is a sports-related concussion.

26. The method of claim 21, wherein said mTBI is caused by a head injury, and wherein said head injury is blunt trauma, acceleration, or deceleration forces.

27. The method of claim 21, wherein said subject is undergoing therapy for said mTBI and method includes monitoring the response to said therapy.

28. The method of claim 21, wherein decreasing levels of SNTF indicates a subsequent decreased risk of long-term neurological dysfunction.

29. The method of claim 25, wherein said subject is a professional sports player.

30. The method of claim 29, wherein the subject is monitored to determine suitabilty for said sports player to return to play.

31. A method for assessing severity of and treating a concussion in a subject having suffered from a concussion, said method comprising:

(a) obtaining a blood, serum, or plasma sample from said subject, within 36 hours of the concussion;

(b) contacting said sample with an antibody that specifically binds to a calpain-generated neoepitope of calpain-cleaved αII-spectrin N-terminal fragment (SNTF), but not to full-length spectrin, to form an antibody-SNTF complex;

(c) measuring the amount of the antibody-SNTF complex, to determine SNTF concentration in the subject's blood, serum or plasma;

(d) comparing the blood, serum or plasma concentration of SNTF in the subject to that of a pre-determined standard;

(e) assessing the severity of the concussion in the subject, wherein an elevated SNTF level in the subject relative to the standard is indicative of the severity of the concussion in the subject; and (f) treating said mTBI in said subject.

32. The method of claim 31, wherein said standard is determined by measuring SNTF levels in a subject or pool of subjects having sustained an orthopedic injury or in a normal uninjured subject or pool of subjects.

33. The method of claim 31, wherein said standard is determined by measuring SNTF levels in a blood, serum, or plasma sample from said subject prior to suffering a concussion.

34. The method of claim 31, wherein said method further comprises the steps of measuring the level of tau in the sample compared to a standard, and the severity assessment for the subject is based on the SNTF and tau levels relative to their respective standards, wherein elevated levels of SNTF, tau, or both relative to their respective standards indicate an elevated risk of long-term neurological dysfunction.

35. The method of claim 31, wherein said subject is further assessed by neuropsychological testing.

36. The method of claim 31, wherein said subject does not undergo a CT scan following said concussion.

37. The method of claim 31, wherein said concussion is a sports-related concussion.

38. The method of claim 31, wherein said concussion is caused by a head injury, and wherein said head injury is blunt trauma, acceleration, or deceleration forces.

39. The method of claim 37, wherein said subject is a professional sports player.

40. The method of claim 39, wherein the severity assessment determines suitabilty for said sports player to return to play.

* * * * *

SEQUENCE LISTING

```
<160> NUMBER OF SEQ ID NOS: 1

<210> SEQ ID NO 1
<211> LENGTH: 1176
<212> TYPE: PRT
<213> ORGANISM: Homo sapiens

<400> SEQUENCE: 1

Met Asp Pro Ser Gly Val Lys Val Leu Glu Thr Ala Glu Asp Ile Gln
1               5                   10                  15

Glu Arg Arg Gln Gln Val Leu Asp Arg Tyr His Arg Phe Lys Glu Leu
            20                  25                  30

Ser Thr Leu Arg Arg Gln Lys Leu Glu Asp Ser Tyr Arg Phe Gln Phe
        35                  40                  45

Phe Gln Arg Asp Ala Glu Glu Leu Glu Lys Trp Ile Gln Glu Lys Leu
    50                  55                  60

Gln Ile Ala Ser Asp Glu Asn Tyr Lys Asp Pro Thr Asn Leu Gln Gly
65                  70                  75                  80

Lys Leu Gln Lys His Gln Ala Phe Glu Ala Glu Val Gln Ala Asn Ser
                85                  90                  95

Gly Ala Ile Val Lys Leu Asp Glu Thr Gly Asn Leu Met Ile Ser Glu
            100                 105                 110

Gly His Phe Ala Ser Glu Thr Ile Arg Thr Arg Leu Met Glu Leu His
        115                 120                 125

Arg Gln Trp Glu Leu Leu Leu Glu Lys Met Arg Glu Lys Gly Ile Lys
    130                 135                 140
```

-continued

```
Leu Leu Gln Ala Gln Lys Leu Val Gln Tyr Leu Arg Glu Cys Glu Asp
145                 150                 155                 160

Val Met Asp Trp Ile Asn Asp Lys Glu Ala Ile Val Thr Ser Glu Glu
                165                 170                 175

Leu Gly Gln Asp Leu Glu His Val Glu Val Leu Gln Lys Lys Phe Glu
            180                 185                 190

Glu Phe Gln Thr Asp Met Ala Ala His Glu Glu Arg Val Asn Glu Val
            195                 200                 205

Asn Gln Phe Ala Ala Lys Leu Ile Gln Glu Gln His Pro Glu Glu Glu
        210                 215                 220

Leu Ile Lys Thr Lys Gln Asp Glu Val Asn Ala Ala Trp Gln Arg Leu
225                 230                 235                 240

Lys Gly Leu Ala Leu Gln Arg Gln Gly Lys Leu Phe Gly Ala Ala Glu
                245                 250                 255

Val Gln Arg Phe Asn Arg Asp Val Asp Glu Thr Ile Ser Trp Ile Lys
            260                 265                 270

Glu Lys Glu Gln Leu Met Ala Ser Asp Asp Phe Gly Arg Asp Leu Ala
            275                 280                 285

Ser Val Gln Ala Leu Leu Arg Lys His Glu Gly Leu Glu Arg Asp Leu
        290                 295                 300

Ala Ala Leu Glu Asp Lys Val Lys Ala Leu Cys Ala Glu Ala Asp Arg
305                 310                 315                 320

Leu Gln Gln Ser His Pro Leu Ser Ala Thr Gln Ile Gln Val Lys Arg
                325                 330                 335

Glu Glu Leu Ile Thr Asn Trp Glu Gln Ile Arg Thr Leu Ala Ala Glu
            340                 345                 350

Arg His Ala Arg Leu Asn Asp Ser Tyr Arg Leu Gln Arg Phe Leu Ala
        355                 360                 365

Asp Phe Arg Asp Leu Thr Ser Trp Val Thr Glu Met Lys Ala Leu Ile
    370                 375                 380

Asn Ala Asp Glu Leu Ala Ser Asp Val Ala Gly Ala Glu Ala Leu Leu
385                 390                 395                 400

Asp Arg His Gln Glu His Lys Gly Glu Ile Asp Ala His Glu Asp Ser
                405                 410                 415

Phe Lys Ser Ala Asp Glu Ser Gly Gln Ala Leu Leu Ala Ala Gly His
            420                 425                 430

Tyr Ala Ser Asp Glu Val Arg Glu Lys Leu Thr Val Leu Ser Glu Glu
        435                 440                 445

Arg Ala Ala Leu Leu Glu Leu Trp Glu Leu Arg Arg Gln Gln Tyr Glu
    450                 455                 460

Gln Cys Met Asp Leu Gln Leu Phe Tyr Arg Asp Thr Glu Gln Val Asp
465                 470                 475                 480

Asn Trp Met Ser Lys Gln Glu Ala Phe Leu Leu Asn Glu Asp Leu Gly
                485                 490                 495

Asp Ser Leu Asp Ser Val Glu Ala Leu Leu Lys Lys His Glu Asp Phe
            500                 505                 510

Glu Lys Ser Leu Ser Ala Gln Glu Glu Lys Ile Thr Ala Leu Asp Glu
        515                 520                 525

Phe Ala Thr Lys Leu Ile Gln Asn Asn His Tyr Ala Met Glu Asp Val
    530                 535                 540

Ala Thr Arg Arg Asp Ala Leu Leu Ser Arg Arg Asn Ala Leu His Glu
545                 550                 555                 560
```

-continued

```
Arg Ala Met Arg Arg Ala Gln Leu Ala Asp Ser Phe His Leu Gln
            565                 570                 575

Gln Phe Phe Arg Asp Ser Asp Glu Leu Lys Ser Trp Val Asn Glu Lys
        580                 585                 590

Met Lys Thr Ala Thr Asp Glu Ala Tyr Lys Asp Pro Ser Asn Leu Gln
            595                 600                 605

Gly Lys Val Gln Lys His Gln Ala Phe Glu Ala Glu Leu Ser Ala Asn
        610                 615                 620

Gln Ser Arg Ile Asp Ala Leu Glu Lys Ala Gly Gln Lys Leu Ile Asp
625                 630                 635                 640

Val Asn His Tyr Ala Lys Asp Glu Val Ala Ala Arg Met Asn Glu Val
                645                 650                 655

Ile Ser Leu Trp Lys Lys Leu Leu Glu Ala Thr Glu Leu Lys Gly Ile
            660                 665                 670

Lys Leu Arg Glu Ala Asn Gln Gln Gln Gln Phe Asn Arg Asn Val Glu
        675                 680                 685

Asp Ile Glu Leu Trp Leu Tyr Glu Val Glu Gly His Leu Ala Ser Asp
    690                 695                 700

Asp Tyr Gly Lys Asp Leu Thr Asn Val Gln Asn Leu Gln Lys Lys His
705                 710                 715                 720

Ala Leu Leu Glu Ala Asp Val Ala Ala His Gln Asp Arg Ile Asp Gly
                725                 730                 735

Ile Thr Ile Gln Ala Arg Gln Phe Gln Asp Ala Gly His Phe Asp Ala
            740                 745                 750

Glu Asn Ile Lys Lys Lys Gln Glu Ala Leu Val Ala Arg Tyr Glu Ala
        755                 760                 765

Leu Lys Glu Pro Met Val Ala Arg Lys Gln Lys Leu Ala Asp Ser Leu
    770                 775                 780

Arg Leu Gln Gln Leu Phe Arg Asp Val Glu Asp Glu Glu Thr Trp Ile
785                 790                 795                 800

Arg Glu Lys Glu Pro Ile Ala Ala Ser Thr Asn Arg Gly Lys Asp Leu
                805                 810                 815

Ile Gly Val Gln Asn Leu Leu Lys Lys His Gln Ala Leu Gln Ala Glu
            820                 825                 830

Ile Ala Gly His Glu Pro Arg Ile Lys Ala Val Thr Gln Lys Gly Asn
        835                 840                 845

Ala Met Val Glu Glu Gly His Phe Ala Ala Glu Asp Val Lys Ala Lys
    850                 855                 860

Leu His Glu Leu Asn Gln Lys Trp Glu Ala Leu Lys Ala Lys Ala Ser
865                 870                 875                 880

Gln Arg Arg Gln Asp Leu Glu Asp Ser Leu Gln Ala Gln Gln Tyr Phe
                885                 890                 895

Ala Asp Ala Asn Glu Ala Glu Ser Trp Met Arg Glu Lys Glu Pro Ile
            900                 905                 910

Val Gly Ser Thr Asp Tyr Gly Lys Asp Glu Asp Ser Ala Glu Ala Leu
        915                 920                 925

Leu Lys Lys His Glu Ala Leu Met Ser Asp Leu Ser Ala Tyr Gly Ser
    930                 935                 940

Ser Ile Gln Ala Leu Arg Glu Gln Ala Gln Ser Cys Arg Gln Gln Val
945                 950                 955                 960

Ala Pro Thr Asp Asp Glu Thr Gly Lys Glu Leu Val Leu Ala Leu Tyr
                965                 970                 975

Asp Tyr Gln Glu Lys Ser Pro Arg Glu Val Thr Met Lys Lys Gly Asp
```

```
                    980               985               990
Ile Leu Thr Leu Leu Asn Ser Thr  Asn Lys Asp Trp Trp  Lys Val Glu
            995                1000               1005

Val Asn  Asp Arg Gln Gly Phe  Val Pro Ala Ala Tyr  Val Lys Lys
    1010                 1015                1020

Leu Asp  Pro Ala Gln Ser Ala  Ser Arg Glu Asn Leu  Leu Glu Glu
    1025                 1030                1035

Gln Gly  Ser Ile Ala Leu Arg  Gln Glu Gln Ile Asp  Asn Gln Thr
    1040                 1045                1050

Arg Ile  Thr Lys Glu Ala Gly  Ser Val Ser Leu Arg  Met Lys Gln
    1055                 1060                1065

Val Glu  Glu Leu Tyr His Ser  Leu Leu Glu Leu Gly  Glu Lys Arg
    1070                 1075                1080

Lys Gly  Met Leu Glu Lys Ser  Cys Lys Lys Phe Met  Leu Phe Arg
    1085                 1090                1095

Glu Ala  Asn Glu Leu Gln Gln  Trp Ile Asn Glu Lys  Glu Ala Ala
    1100                 1105                1110

Leu Thr  Ser Glu Glu Val Gly  Ala Asp Leu Glu Gln  Val Glu Val
    1115                 1120                1125

Leu Gln  Lys Lys Phe Asp Asp  Phe Gln Lys Asp Leu  Lys Ala Asn
    1130                 1135                1140

Glu Ser  Arg Leu Lys Asp Ile  Asn Lys Val Ala Glu  Asp Leu Glu
    1145                 1150                1155

Ser Glu  Gly Leu Met Ala Glu  Glu Val Gln Ala Val  Gln Gln Gln
    1160                 1165                1170

Glu Val  Tyr
    1175
```